United States Patent
Grammenos et al.

(10) Patent No.: US 6,211,190 B1
(45) Date of Patent: Apr. 3, 2001

(54) PYRIMIDINE DERIVATIVES, PROCESS AND INTERMEDIATE PRODUCTS FOR THEIR PREPARATION AND PESTICIDES OR FUNGICIDES CONTAINING THESE DERIVATIVES

(75) Inventors: Wassilios Grammenos, Ludwigshafen; Herbert Bayer, Mannheim; Thomas Grote, Schifferstadt; Reinhard Kirstgen, Neustadt; Bernd Müller, Frankenthal; Ruth Müller, Friedelsheim; Klaus Oberdorf, Heidelberg; Arne Ptock, Ludwigshafen; Hubert Sauter, Neckarpromenade; Franz Röhl, Schifferstadt; Michael Rack, Heidelberg; Gisela Lorenz, Hambach; Eberhard Ammermann, Heppenheim; Siegfried Strathmann, Limburgerhof; Volker Harries, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/117,707

(22) PCT Filed: Jan. 31, 1997

(86) PCT No.: PCT/EP97/00423

§ 371 Date: Aug. 4, 1998

§ 102(e) Date: Aug. 4, 1998

(87) PCT Pub. No.: WO97/29093

PCT Pub. Date: Aug. 14, 1997

(30) Foreign Application Priority Data

Feb. 5, 1996 (DE) .............................. 196 03 990

(51) Int. Cl.⁷ .................. A01N 43/54; C07D 239/30; C07D 239/34; C07D 239/37
(52) U.S. Cl. .................. 514/269; 514/274; 544/310; 544/311; 544/316; 544/318; 544/319; 544/322; 544/333; 544/335
(58) Field of Search .................. 544/300, 310, 544/321, 319, 302, 284, 311, 314, 316, 318, 322, 333, 335; 514/252, 259, 274, 272, 316, 317, 324, 321, 269

(56) References Cited

U.S. PATENT DOCUMENTS

| | | | |
|---|---|---|---|
| 5,145,980 | 9/1992 | Wenderoth et al. | 560/35 |
| 5,194,662 | 3/1993 | Brand et al. | 560/35 |
| 5,286,750 | 2/1994 | Mueller et al. | 514/546 |
| 5,298,527 | 3/1994 | Grammenos et al. | 514/539 |
| 5,416,068 | 5/1995 | Grammenos et al. | 504/378 |
| 5,536,734 | 7/1996 | Mueller et al. | 514/336 |
| 5,807,863 | * 9/1998 | Eberle et al. | 514/269 |

FOREIGN PATENT DOCUMENTS

| | | |
|---|---|---|
| 2005345 | 6/1990 | (CA) . |
| 2043733 | 6/1991 | (CA) . |
| 178826 | 4/1986 | (EP) . |
| 634405 | 1/1995 | (EP) . |
| 667343 | 8/1995 | (EP) . |
| 2172595 | 9/1986 | (GB) . |
| 92/18487 | 10/1992 | (WO) . |

OTHER PUBLICATIONS

Hutchings et al., *Tetrahedron*, 44 (12), 1988, 3727–3734.

* cited by examiner

Primary Examiner—Richard L. Raymond
(74) Attorney, Agent, or Firm—Keil & Weinkauf

(57) ABSTRACT

Pyrimidine compounds I

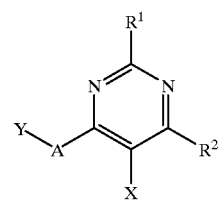

wherein

X is $C(CO_2CH_3)=NOCH_3$, $C(CONHCH_3)=NOCH_3$, $C(CO_2CH_3)=CHOCH_3$, $C(CO_2CH_3)=CHCH_3$ or $N(CO_2CH_3)-OCH_3$;

$R^1$, $R^2$ are hydrogen, alkyl, haloalkyl or alkoxy;

A is

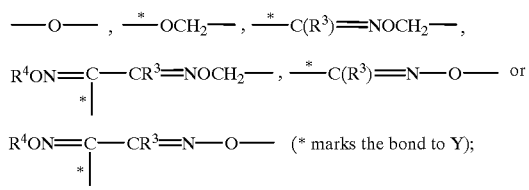

$R^3$ is hydrogen, alkyl, haloalkyl, phenoxyalkyl, cycloalkyl, cyano, alkoxy, hydroxyl or halogen;

$R^4$ is hydrogen, optionally substituted alkyl, alkenyl, alkynyl, haloalkenyl, haloalkynyl, cycloalkyl or alkoxy;

Y is hydrogen, hydroxyl, halogen, optionally substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio, or their salt, their synthesis and intermediates therefore, and their activity against fungi or animal pests.

29 Claims, No Drawings

PYRIMIDINE DERIVATIVES, PROCESS AND INTERMEDIATE PRODUCTS FOR THEIR PREPARATION AND PESTICIDES OR FUNGICIDES CONTAINING THESE DERIVATIVES

This application is a 371 of PCT/EP97/00423, filed Jan. 31, 1997.

The present invention relates to pyrimidine derivatives of the formula I

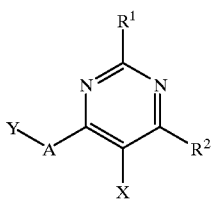

where the substituents have the following meanings:

X is $C(CO_2CH_3)=NOCH_3$, $C(CONHCH_3)=NOCH_3$, $C(CO_2CH_3)=CHOCH_3$, $C(CO_2CH_3)=CHCH_3$, $N(CO_2CH_3)-OCH_3$;

$R^1$ and $R^2$ independently of one another are hydrogen, $C_1-C_4$-alkyl, $C_1-C_4$-haloalkyl or $C_1-C_4$-alkoxy;

A is

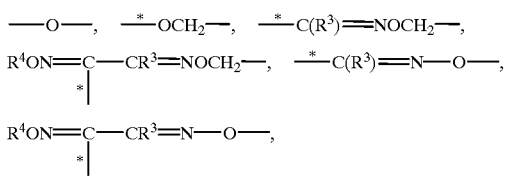

where the bond marked by * is to Y;

$R^3$ is hydrogen, $C_1-C_4$-alkyl, $C_1-C_4$-haloalkyl, phenoxy-$C_1-C_4$-alkyl, $C_3-C_6$-cycloalkyl, cyano, $C_1-C_4$-alkoxy, hydroxyl, halogen;

$R^4$ is hydrogen, $C_1-C_8$-alkyl, $C_1-C_4$-haloalkyl, $C_1-C_6$-cyanoalkyl, $C_1-C_4$-alkoxy-$C_1-C_4$-alkyl, $C_2-C_4$-alkenyloxy-$C_1-C_4$-alkyl, $C_1-C_4$-halo-alkoxy-$C_1-C_4$-alkyl, $C_1-C_4$-oxoalkyl, $C_2-C_4$-alkenyl, $C_2-C_4$-alkynyl, $C_2-C_4$-haloalkenyl, $C_2-C_4$-haloalkynyl, $C_3-C_6$-cycloalkyl, $C_3-C_6$-cycloalkyl-$C_1-C_4$-alkyl, $C_1-C_4$-alkoxy;

Y is hydrogen, hydroxyl, halogen, unsubstituted or substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio, where if X is $C(CO_2CH_3)=CHOCH_3$ A is not —O—, or its salts.

Preferred compounds of the formula I, are those where the substituents have the following meanings:

X is $C(CO_2CH_3)=NOCH_3$, $C(CONHCH_3)=NOCH_3$, $C(CO_2CH_3)=CHOCH_3$, $C(CO_2CH_3)=CHCH_3$, $N(CO_2CH_3)-OCH_3$;

$R^1$ and $R^2$ independently of one another are hydrogen, $C_1-C_4$-alkyl, $C_1-C_4$-haloalkyl or $C_1-C_4$-alkoxy;

A is

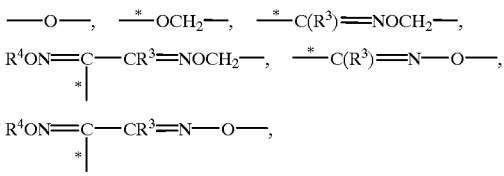

where the bond marked by * is to Y;

$R^3$ is hydrogen, $C_1-C_4$-alkyl, $C_1-C_4$-haloalkyl, phenoxy-$C_1-C_4$-alkyl, $C_3-C_6$-cycloalkyl, cyano, hydroxyl, halogen;

$R^4$ is hydrogen, $C_1-C_4$-alkyl, $C_1-C_4$-haloalkyl, $C_2-C_4$-alkenyl, $C_2-C_4$-alkynyl, $C_2-C_4$-haloalkenyl, $C_2-C_4$-haloalkynyl, $C_3-C_6$-cycloalkyl, $C_1-C_4$-alkoxy;

Y is unsubstituted or substituted aryl, hetaryl, cycloalkyl, cycloalkenyl, heterocyclyl, alkyl, haloalkyl or alkoxy, where if X is $C(CO_2CH_3)=CHOCH_3$ A is not —O—, and their salts.

Especially preferred compounds of the formula 1 as claimed in claim 1 are those where the substituent Y has the following meanings:

hydrogen, hydroxyl, halogen, $C_1-C_4$-alkyl, $C_2-C_4$-alkenyl, $C_2-C_4$-alkynyl, $C_1-C_4$-haloalkyl, $C_1-C_4$-alkoxy, $C_1-C_4$-alkoxy-$C_1-C_4$-alkyl, $C_3-C_6$-cycloalkyloxy, $C_1-C_4$-alkylthio, $C_3-C_6$-cycloalkyl, $C_5-C_8$-cycoalkenyl, heterocyclyl, aryl, aryloxy, arylthio, aryl-$C_1-C_4$-alkyl, aryl-$C_2-C_4$-alkenyl, aryloxy-$C_1-C_4$-alkyl, aryl-$C_1-C_4$-alkoxy, hetaryl, hetaryloxy, hetarylthio, hetaryl-$C_1-C_4$-alkyl, hetarylthio-$C_1-C_4$-alkyl, hetaryl-$C_1-C_4$-alkoxy or hetaryl-$C_2-C_4$-alkenyl, where the cyclic radicals can be partially or completely halogenated and/or can carry 1 to 3 of the following groups:

cyano, nitro, hydroxyl, mercapto, amino, formyl, carboxyl, aminocarbonyl, aminothiocarbonyl, $C_1-C_{12}$-alkyl, $C_1-C_6$-haloalkyl, $C_1-C_6$-hydroxyalkyl, $C_1-C_6$-alkylsulfonyl, $C_1-C_6$-alkylsulfoxyl, $C_3-C_6$-cycloalkyl, $C_1-C_6$-alkoxy, $C_1-C_6$-haloalkoxy, $C_1-C_6$-alkylcarbonyl, $C_1-C_6$-alkylcarbonyloxy, $C_1-C_6$-alkoxycarbonyl, benzyloxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, $C(=NOR^b)-Z_n-R^c$, $NR^f-CO-D-R^g$, benzyl, benzyloxy, aryl, aryloxy, hetaryl or hetaryloxy, where the 6 last mentioned radicals can be partially or completely halogenated and/or can carry 1 to 3 of the following groups: cyano, $C_1-C_6$-alkyl, $C_1-C_6$-alkoxy-carbonyl, $C_1-C_4$-alkoxy, nitro, $C_1-C_6$-alkylcarbonyl, $C_1-C_6$-haloalkyl, hydroxy, rhodano, formyl, aminocarbonylamino, methylsulfonylamino, aminocarbonyl, $C_1-C_6$-alkylaminocarbonyl;

Z is oxygen, sulfur or nitrogen, the nitrogen bearing hydrogen or $C_1-C_6$-alkyl;

D is a direct bond, oxygen or $NR^h$;

n is 0 or 1;

$R^b$ and $R^c$ independently of one another are hydrogen, $C_1-C_6$-alkyl, $C_2-C_6$-alkenyl, $C_2-C_6$-alkynyl or benzyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$ and $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl or hetaryl-$C_1$–$C_6$-alkyl, $R^o$ hydrogen or $C_1$–$C_6$-alkyl.

Particulary preferred compounds are those where the substituent Y has the following meanings:

$C_1$–$C_4$-alkyl, $C_1$–$C_4$-haloalkyl, $C_1$–$C_4$-alkoxy, $C_3$–$C_6$-cycloalkyl, $C_5$–$C_8$-cycoalkenyl, heterocyclyl, aryl or hetaryl, where the cyclic radicals can be partially or completely halogenated and/or can carry 1 to 3 of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$Z_n$—$R^c$ or $NR^f$—CO—D—$R^o$;

Z is oxygen, sulfur or nitrogen, the nitrogen bearing hydrogen or $C_1$–$C_6$-alkyl;

D is a direct bond, oxygen or $NR^h$;

n is 0 or 1;

$R^b$ and $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$ and $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl or hetaryl-$C_1$–$C_6$-alkyl.

The invention additionally relates to processes and intermediates for preparing these compounds and to compositions comprising them for controlling animal pests and harmful fungi.

Phenylacetic acid derivatives for controlling pests are disclosed in the literature (EP-A 422 597; EP-A 463 488; EP-A 370 629; EP-A 460 575; EP-A 472 300; WO-A 90/07,493; WO-A 92/13,830; WO-A 92/18,487; WO-A 95/18,789; WO-A 95/21,153; WO-A 95/21,154; WO-A 95/21,156).

Pyrimidine derivatives for controlling pests are furthermore disclosed in the literature (EP-A 634 405).

It is an object of the present invention to provide novel compounds having an improved action.

We have found that this object is achieved by the pyrimidine derivatives I defined at the outset. We have additionally found processes and intermediates for their preparation and compositions comprising them for controlling animal pests and harmful fungi, and their use in this context.

The compounds I are obtainable in various ways by methods known per se in the literature.

Fundamentally, it is insignificant in the synthesis of the compounds whether the group X or the group Y—A— is synthesized first.

The synthesis of the group X is disclosed, for example, in the literature cited at the outset and in EP-A 178 826, EP-A 493 711, EP-A 534 216, EP-A 658 541, EP-A 658 542 and EP-A 658 543.

The novel pyrimidines of the formula I, where X is $C(CO_2CH_3)=NOCH_3$ or $C(CONHCH_3)=N—OCH_3$, are thus obtained, for example, by reacting an α-oxopyrimidinylacetic acid derivative of the formula IIa

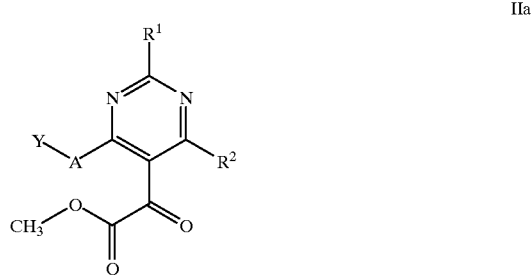

IIa where Y, A, $R^1$ and $R^2$ have the meanings indicated above, in a manner known per se (EP-A-493 711) with methoxyamine ($CH_3O$—$NH_2$) or methoxyamine hydrohalide, if appropriate in the presence of a diluent and if appropriate in the presence of a reaction auxiliary ($X=C(CO_2CH_3)=N—OCH_3$), or by reacting the 2-oximinopyrimidinylacetic acid derivatives of the formula IIb

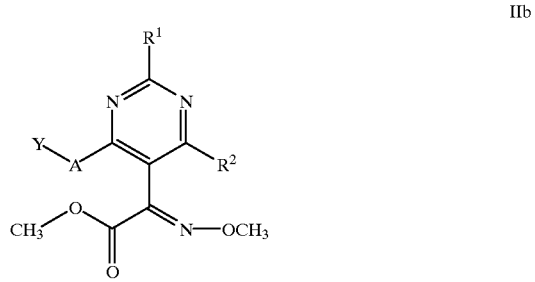

IIb in a manner known per se (EP-A-477 631) with methylamine, if appropriate in the presence of a diluent and if appropriate in the presence of a reaction auxiliary ($X=C(CONHCH_3)=N—OCH_3$).

Compounds of the general formula I where A, Y, $R^1$ and $R^2$ have the meanings indicated above, and X is $C(CO_2CH_3)=CHOCH_3$ or $C(CO_2CH_3)=CH—CH_3$, are obtained, for example, by reacting the compounds of the formula IIa in a manner known per se (EP-A-513 580; Tetrahedron 3727 (1988); GB 2172595) with a Wittig reagent of the formula IIc or IId.

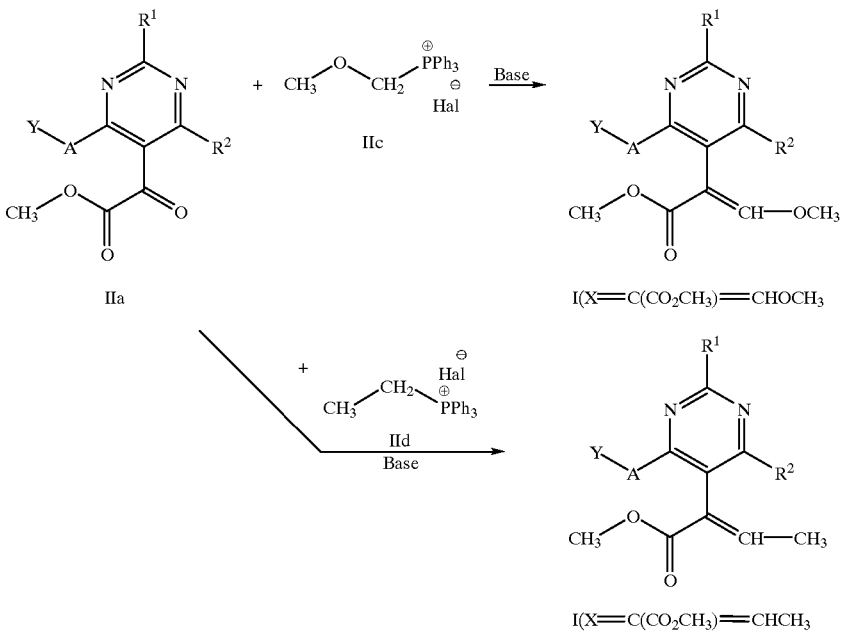

Hal in the formulae IIc and IId is iodine, bromine, chlorine or fluorine, preferably iodine, bromine or chlorine; Ph is phenyl.

Alternatively, the pyrimidines of the formula I where X, Y, $R^1$ and $R^2$ have the meanings indicated and A is oxygen,

can also be obtained by reacting the halopyrimidine derivatives of the formula III

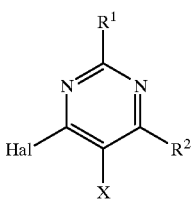

where Hal is bromine, chlorine or fluorine, preferably chlorine or fluorine, with nucleophiles of the formula Y—A—H (IIIa), where Y and A have the meanings indicated, if appropriate in the presence of a diluent and if appropriate in the presence of a reaction auxiliary.

Alternatively, the pyrimidines of the formula I where X, Y, $R^1$ and $R^2$ have the meanings indicated and A is

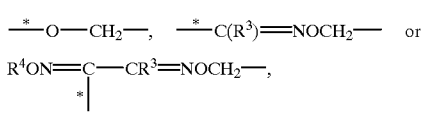

$R^3$ and $R^4$ having the meanings indicated above, can thus also be obtained by reacting the halopyrimidine derivatives of the formula IV

IV in a similar manner to processes known from the literature (EP-A-513 580; EP-A-400 417; DE-A-4 020 384; WO-A-95/21153), with nucleophiles of the formula Y—B—H (IVa) where Y has the meanings indicated and B is

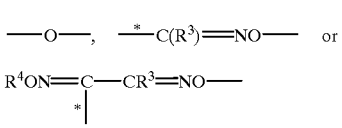

$R^3$ and $R^4$ having the meanings indicated, if appropriate in the presence of a diluent and if appropriate in the presence of a reaction auxiliary. Hal is iodine, bromine or chlorine, preferably bromine or chlorine.

Compounds of the general formula I where A, Y, $R^1$ and $R^2$ have the meanings indicated above and X is $N(CO_2CH_3)$—$OCH_3$ are obtained by converting nitropyrimidine derivatives of the formula V

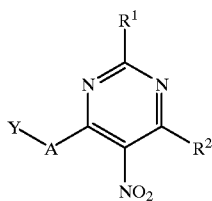

V in a manner similar to processes known from the literature (WO 93/15046) into the corresponding methoxycarbamates of the formula I (X=N(CO$_2$CH$_3$)—OCH$_3$).

This is expediently carried out by first reducing a nitropyrimidine derivative of the formula V in a manner known per se to the corresponding N-hydroxyaminopyrimidine of the formula X

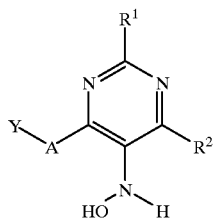

X and then reacting X with a carbonyl compound of the formula XIII

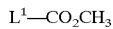        XIII where L$^1$ is a nucleophilically replaceable group, to give the pyrimidinecarbamate XIV

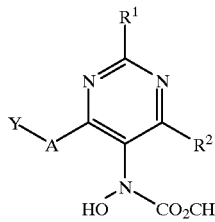

XIV and then reacting XIV in a manner known per se with a reagent of the formula XV

        XV where L$^2$ is a nucleophilically replaceable group, with formation of the compound I (X=N(CO$_2$CH$_3$)OCH$_3$).

L$^1$ and L$^2$ are, for example, halogen, e.g. chlorine, bromine or iodine, or alkyl- or arylsulfonate, e.g. methylsulfonate, trifluoromethylsulfonate, phenylsulfonate or methylphenylsulfonate.

The reduction of V to the hydroxylamine X is customarily carried out at from −30° C. to 80° C., preferably 0° C. to 60° C., in an inert organic solvent in the presence of a catalyst [cf. *Ann. Chem.* 316, 278 (1901); EP-A 085 890; DE-A 19 50 27 00].

The reaction of the hydroxylamine X with XIII is customarily carried out at from −20° C. to 60° C., preferably 0° C. to 30° C., in an inert organic solvent in the presence of a base [cf. WO-A 93/15046]. The reaction of the pyrimidinecarbamate XIV with XV is customarily carried out at from −20° C. to 80° C., preferably 0° C. to 60° C., in an inert organic solvent in the presence of a base [cf. WO-A 93/15046].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably cyclohexane, toluene, methylene chloride, tert-butyl methyl ether and water. Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides, such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate, and alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, and alkali metal and alkaline earth metal alkoxides such as sodium methoxide, sodium ethoxide, potassium ethoxide, potassium tert-butoxide and dimethoxymagnesium, additionally organic bases, e.g. tertiary amines such as trimethylamine, triethylamine, triisopropylethylamine and N-methylpiperidine, pyridine, substituted pyridines such as collidine, lutidine and 4-dimethylaminopyridine, and bicyclic amines. Potassium carbonate, sodium hydroxide and triethylamine are particularly preferred.

In generaly, the bases are employed in catalytic amounts, but they can also be used in equimolar amounts, in excess or, if appropriate, as solvents.

The starting compounds of the general formulae IIa, III, IV and V are still unknown, and as novel substances are likewise a subject of the present application.

Novel compounds of the general formulae IIa, where Y, R$^1$ and R$^2$ have the meanings indicated above and A is oxygen, —C(R$^3$)=NO— or

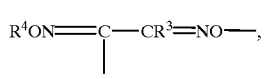

are obtained, for example, according to the following reaction scheme:

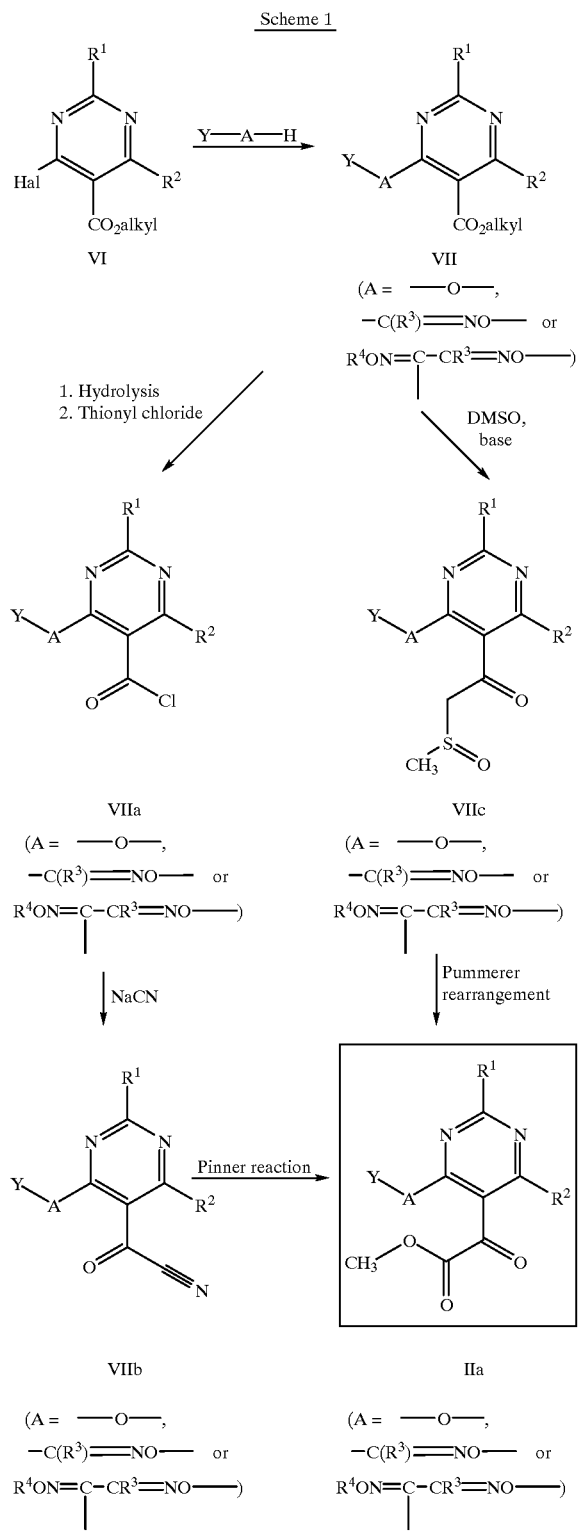

Scheme 1

Y has the meanings indicated above and
A is oxygen, $$-*C(R^3)=NO- \quad \text{or} \quad R^4ON=C-CR^3=NO-$$
$$\phantom{-*C(R^3)=NO-\quad \text{or} \quad R^4ON=C-CR^3=NO}*|$$

or with alkali metal salts of the formula Y—A—M, where M is expediently sodium, potassium or lithium, if appropriate in the presence of a reaction auxiliary, such as, for example, copper(I) chloride, and if appropriate in the presence of a diluent.

Suitable diluents are, for example, aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone, and tert-butyl methyl ketone, and also dimethyl sulfoxide and dimethylformamide, particularly preferably acetone, dimethylformamide, tetrahydrofuran and dimethyl sulfoxide. Mixtures of the solvents mentioned can also be used.

The process can also be carried out in a two-phase system, such as, for example, water/toluene or water/dichloromethane, if appropriate in the presence of a phase-transfer catalyst, such as, for example, tetrabutylammonium iodide, tetrabutylammonium bromide, tetrabutylammonium chloride, trimethylbenzylammonium chloride, 15-crown-5, 18-crown-6 or tris[2-(2-methoxyethoxy)-ethyl]amine. The process is preferably carried out in the presence of a suitable inorganic or organic base.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate, and alkali metal hydrogen carbonates such as sodium hydrogen carbonate, organometallic compounds, in particular alkali metal alkyls such as methyllithium, butyllithium and phenyllithium, alkylmagnesium halides such as methyl magnesium chloride, and alkali metal and alkaline earth metal alkoxides such as sodium methoxide, sodium ethoxide, potassium ethoxide, potassium tert-butoxide and dimethoxymagnesium, additionally organic bases, e.g. tertiary amines such as trimethylamine, triethylamine, triisopropylethylamine and N-methylpiperidine, pyridine, substituted pyridines such as collidine, lutidine and 4-dimethylaminopyridine, and bicyclic amines. Potassium carbonate, sodium hydroxide, triethylamine and sodium methoxide are particularly preferred.

In general, the bases are employed in catalytic amounts, but they can also be used in equimolar amounts, in excess or, if appropriate, as solvents.

When carrying out the process described above, the temperatures can be varied within a wide range. In general, the process is carried out at from 0 to 150° C., preferably from 20 to 130° C.

The process is customarily carried out at normal pressure. However, it is also possible to work at elevated or reduced pressure.

The pyrimidine derivatives of the formula VI are known from the literature and/or can be prepared by processes known per se [J. Chem. Soc. 364 (1937); Chem. Pharm. Bull. 2354 (1971); JOC 2137 (1960); Chem. Ber. 803 (1962)]. Alkyl is expediently $C_1$–$C_4$-alkyl, such as, for example, methyl, ethyl, or n-propyl. These can then be reacted with nucleophiles of the formula Y—A—H, where To carry out the process described above, in general from 1.0 to 3.0 mol, preferably 1.0 to 2.0 mol, of nucleophile Y—A—H and, if appropriate from 1.0 to 3.0 mol, preferably 1.0 to 2.0 mol, of reaction auxiliary are employed per mole of VI.

The acid chlorides VIIa are expediently obtained from the compounds VII by first hydrolyzing the carbalkoxy group of VII in a manner known per se in a first step and expediently converting the carboxylic acid obtained in a manner known per se into the acid chloride VIIa using thionyl chloride (Houben-Weyl, Supplementary Volume 5, p. 225ff, p. 59ff and p. 604ff.).

The pyrimidinecarbonyl cyanides of the formula VIIb are obtained by reacting the acid chlorides of the formula VIIa with metal cyanides, for example with copper(I) or sodium cyanide, if appropriate in the presence of a diluent, such as, for example, acetonitrile, in a manner known per se, expediently at from 10 to 100° C. (EP-A-493 711).

The α-oxo-pyrimidinylacetic acid derivatives of the formula IIa are expediently obtained by hydrolyzing the pyrimidinecarbonyl cyanides of the formula VIIb with aqueous acids, for example with hydrochloric acid, at from 10 to 100° C., then esterifying these by reaction with alcohols, for example methanol, if appropriate in the presence of a reaction auxiliary, such as, for example, sulfuric acid, and if appropriate in the presence of diluents, such as, for example, toluene, at from 10 to 150° C., analogously to known processes (EP-A-493 711).

Alternatively, α-oxo-pyrimidinylacetic acid derivatives of the formula IIa are obtained by reacting β-ketosulfoxides of the formula VIIc with a halogenating agent, for example N-bromosuccinimide, if appropriate in the presence of a diluent, such as, for example, acetone, and then treating in a manner known per se with an alcohol, such as, for example, methanol, at from 0 to 150° C. (EP-A-493 711).

Compounds of the general formula IIa where Y, $R^1$ and $R^2$ have the meanings indicated above, and A is —O—$CH_2$—, —$C(R^3)$=$NOCH_2$— or

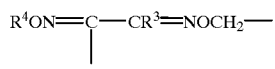

are obtained according to the following reaction scheme:

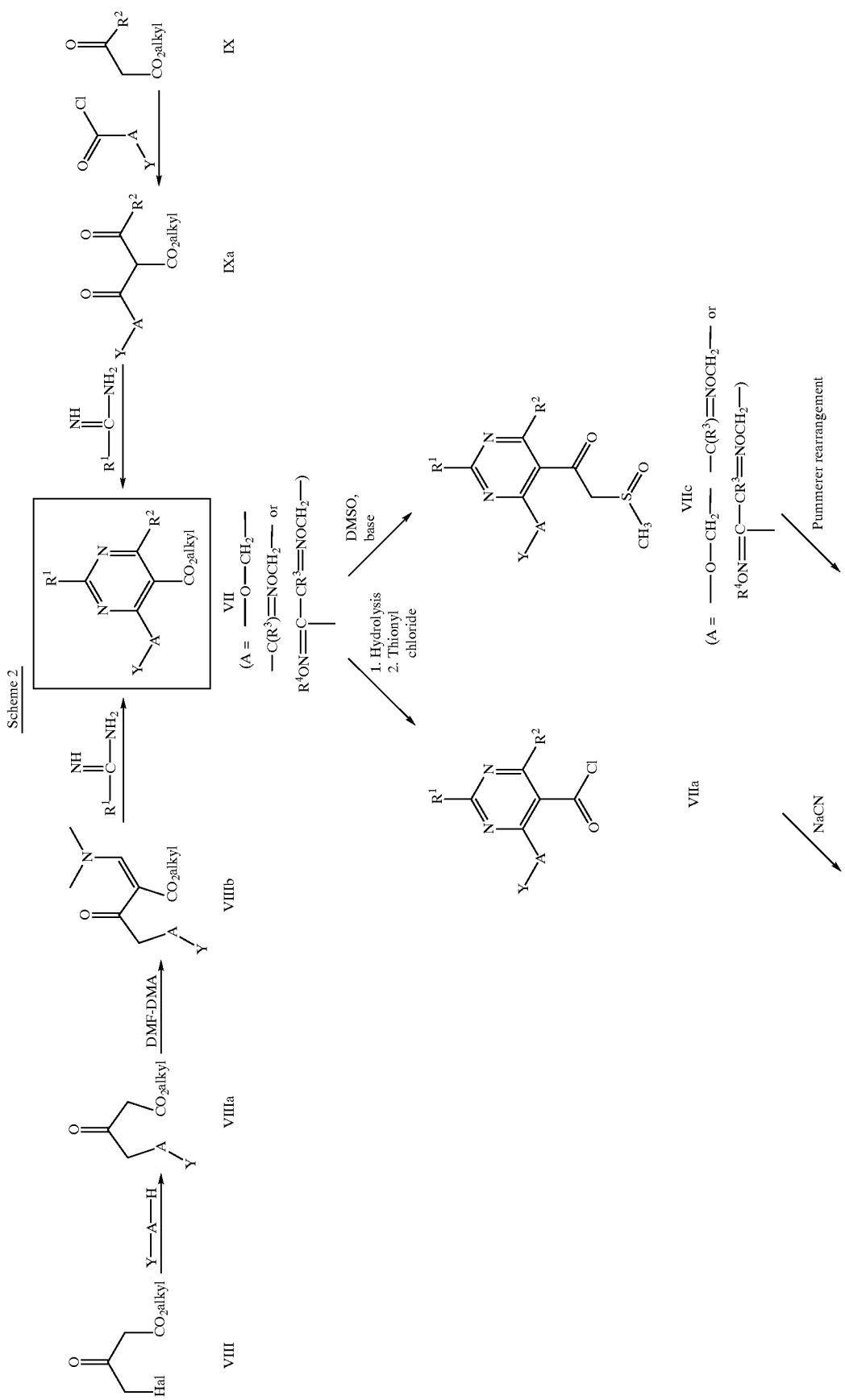

-continued
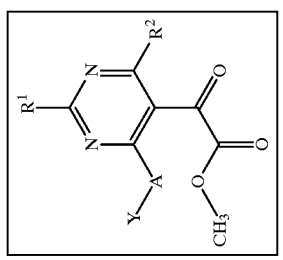
IIa
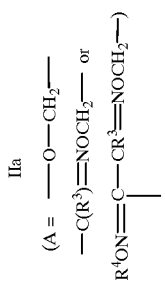
↑ Pinner reaction
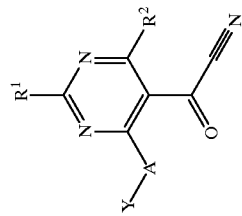
VIIb
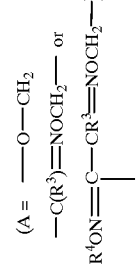

The pyrimidinecarboxylic acid esters of the formula VII, where Y and $R^1$ have the meanings indicated above, A is —O—$CH_2$—, —$C(R^3)$=$NOCH_2$— or

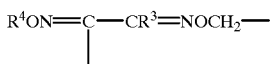

and $R^2$ is hydrogen, are obtained by reacting the dimethylaminomethylene derivatives of the formula VIIIb with amidines of the formula $R^1$—$C(NH_2)$=NH or $R^1$—$C(NH_2)$=NH hydrohalide, if appropriate in the presence of a diluent and if appropriate in the presence of a reaction auxiliary, in a manner similar to processes known from the literature [J.Heterocyclic Chem. 295 (1990); Farmaco, Ed. Sci. 48, 335 (1993); Heterocycles 1375 (1994)].

The dimethylaminomethylene derivatives of the formula VIIIb are known or can be prepared by processes known from the literature [J. Heterocyclic Chem. 21, 301 (1984)].

The acetoacetic ester derivatives of the formula VIIIa are also either known or can be prepared by a process known per se [J. Chem. Soc. 529 (1979)] if the halogen derivatives of the formula VIII, where Hal is bromine or chlorine, are reacted with nucleophiles of the formula Y—A—H, where Y has the meanings indicated above and
A is

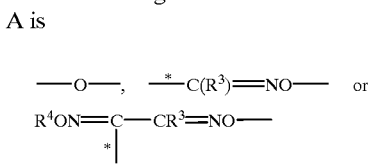

The pyrimidinecarboxylic acid esters of the formula VII where Y and $R^1$ have the meanings indicated above, A is —O—$CH_2$—, —$C(R^3)$=$NOCH_2$— or

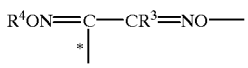

and $R^2$ is not hydrogen, are obtained by reacting the carbonyl derivatives of the formula IXa with amidine derivatives of the formula $R^1$—$C(NH_2)$=NH or $R^1$—$C(NH_2)$=NH hydrohalide, if appropriate in the presence of a diluent and if appropriate in the presence of a reaction auxiliary in a manner similar to processes known from the literature (J. Heterocyclic Chem. 27, 295 (1990)).

The carbonyl derivatives of the formula IXa are known or can be prepared by a process known per se [J. Heterocyclic Chem. 21, 301 (1984)] by reacting the β-keto esters of the formula IX with a carbonyl chloride of the formula Y—A—C—(Cl)=O.

The further conversion of the pyrimidinecarboxylic acid esters of the formula VII into the α-oxo-pyrimidinyl acetic acid derivatives of the formula IIa, where Y, $R^1$ and $R^2$ have the meanings indicated above and A is —O—$CH_2$—, —$C(R^3)$=$NOCH_2$— or

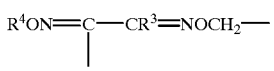

is then carried out correspondingly as described for scheme 1.

The nitropyrimidine derivatives of the formula V, where Y, $R^1$ and $R^2$ have the meanings indicated above and A is oxygen, —$C(R^3)$=NO— or

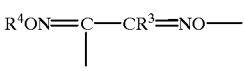

are obtained according to the following reaction scheme:

Scheme 3

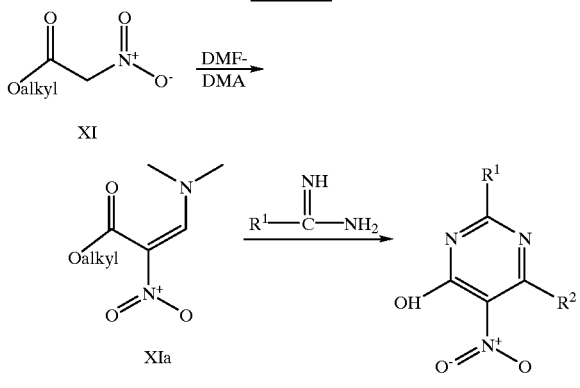

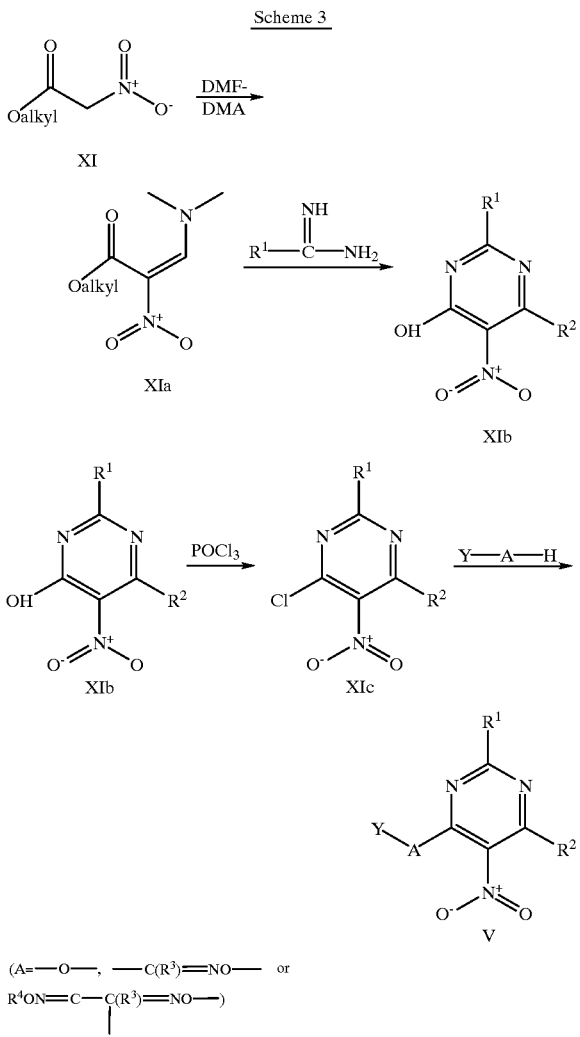

The nitropyrimidine derivatives of the formula V, where Y, $R^1$ and $R^2$ have the meanings indicated above and A is oxygen, —$C(R^3)$=NO— or

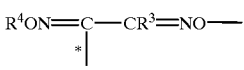

can be prepared from the halopyrimidine derivatives of the formula XIc according to processes known per se by reacting these with nucleophiles of the formula Y—A—H, where Y has the meanings indicated above, A is oxygen, —$C(R^3)$=NO— or

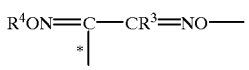

or with alkali metal salts of the formula Y—A—M, where M is sodium, potassium or lithium, if appropriate in the presence of a reaction auxiliary, such as, for example, copper(I) chloride, and if appropriate in the presence of a diluent.

Suitable diluents are, for example, aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably tetrahydrofuran, acetone, dimethylformamide, acetonitrile and dimethyl sulfoxide. Mixtures of the solvents mentioned can also be used.

The process can also be carried out in a two-phase system, such as, for example, water/toluene or water/dichloromethane, if appropriate in the presence of a phase-transfer catalyst, such as, for example, tetrabutylammonium iodide, tetrabutylammonium bromide, tetrabutylammonium chloride, trimethylbenzylammonium chloride, 15-crown-5, 18-crown-6 or tris[2-(2-methoxyethoxy)-ethyl]amine. The process is preferably carried out in the presence of a suitable inorganic or organic base.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate, and alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, and alkali metal and alkaline earth metal alkoxides such as sodium methoxide, sodium ethoxide, potassium ethoxide, potassium tert-butoxide and dimethoxymagnesium, additionally organic bases, e.g. tertiary amines such as trimethylamine, triethylamine, triisopropylamine and N-methylpiperidine, pyridine, substituted pyridines such as collidine, lutidine and 4-dimethylaminopyridine, and bicyclic amines. Potassium carbonate, sodium hydroxide, triethylamine and sodium methoxide are particularly preferred.

In general, the bases are employed in catalytic amounts, but they can also be used in equimolar amounts, in excess or, if appropriate, as solvents.

When carrying out the process described above, the temperatures can be varied within a wide range. In general, the process is carried out at from 0 to 150° C., preferably from 20 to 130° C.

The process is customarily carried out at normal pressure. However, it is also possible to work at elevated or reduced pressure.

To carry out the process described above, in general from 1.0 to 3.0 mol, preferably 1.0 to 2.0 mol, of nucleophile Y—A—H and, if appropriate, from 1.0 to 3.0 mol, preferably 1.0 to 2.0 mol, of reaction auxiliary are employed per mole of XIc.

The reaction is carried out and worked up and the products are isolated according to methods known per se.

The halopyrimidine derivatives of the formula XIc where $R^1$ and $R^2$ have the meanings indicated above can be prepared from the corresponding hydroxypyrimidine derivatives of the formula XIb according to a process known per se, e.g. by reaction with $POCl_3$.

The hydroxypyrimidine derivatives of the formula XIb are either known or can be prepared from the compounds of the formula XIa by reaction with amidines of the formula $R^1$—$C(NH_2)$=NH or $R^1$—$C(NH_2)$=NH hydrohalide, if appropriate in the presence of a diluent and if appropriate in the presence of a reaction auxiliary in a manner similar to processes known from the literature [Khim. Farm. Zh, 25 (9) 62 (1991)].

The nitropyrimidine derivatives of the formula V, where Y, $R^1$ and $R^2$ have the meanings indicated above and A is —O—$CH_2$—, —$C(R^3)$=$NOCH_2$— or

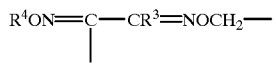

are obtained according to the following reaction scheme:

Scheme 4

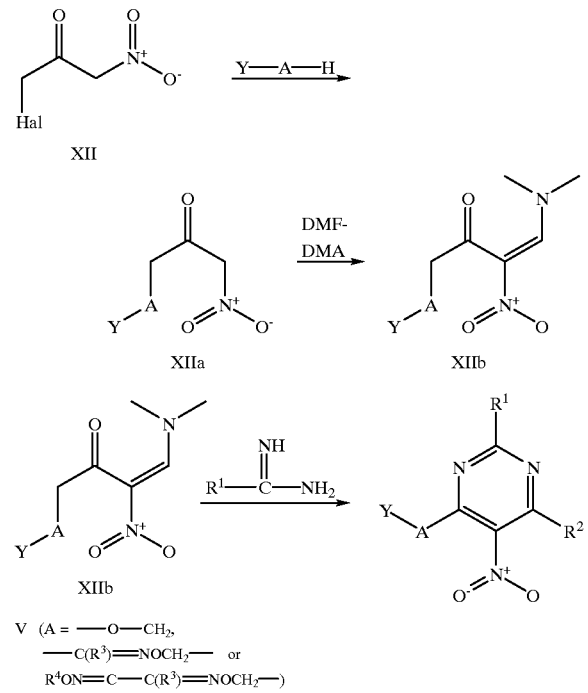

V (A = —O—$CH_2$,
  —$C(R^3)$=$NOCH_2$— or
  $R^4ON$=C—$C(R^3)$=$NOCH_2$—)

The nitropyrimidine derivatives of the formula V, where Y, $R^1$ and $R^2$ have the meanings indicated above and A is —O—$CH_2$—, —$C(R^3)$=$NOCH_2$— or

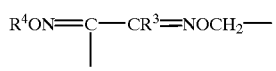

can be prepared from the dimethylaminomethylene derivatives of the formula XIIb according to a process known per se by reacting these with amidine derivatives of the formula $R^1$—$C(NH_2)$=NH or $R^1$—$C(NH_2)$=NH hydrohalide, if appropriate in the presence of a diluent and if appropriate in the presence of a reaction auxiliary, in a manner similar to processes known from the literature (J. Heterocyclic Chem. 27, 295 (1990)).

The dimethylaminomethylene derivatives of the formula XIIb can be prepared from the halonitro derivatives of the formula XII which are known or accessible by processes known per se, Hal in the formula XII expediently being bromine or chlorine, by reaction with nucleophiles of the formula Y—A—H where Y has the meanings indicated above and

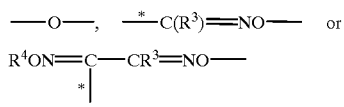

or by reaction with alkali metal salts of the formula Y—A—M, where M is sodium, potassium or lithium, if appropriate in the presence of a reaction auxiliary, such as, for example, copper(I) chloride, and if appropriate in the presence of a diluent.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and dimethyl sulfoxide and dimethylformamide, particularly preferably tetrahydrofuran, acetone, dimethylformamide, acetonitrile and dimethyl sulfoxide. Mixtures of the solvents mentioned can also be used.

The process can also be carried out in a two-phase system, such as, for example, water/toluene or water/dichloromethane, if appropriate in the presence of a phase-transfer catalyst, such as, for example, tetrabutylammonium chloride, 15-crown-5, 18-crown-6 or tris[2-(2-methoxyethoxy)ethyl]amine. The process is preferably carried out in the presence of a suitable inorganic or organic base.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate, and alkali metal hydrogen carbonates such as sodium hydrogen carbonate, organometallic compounds, in particular alkali metal alkyls such as methyl lithium, butyl lithium and phenyl lithium, alkylmagnesium halides such as methylmagnesium chloride, and alkali metal and alkaline earth metal alkoxides such as sodium methoxide, sodium ethoxide, potassium ethoxide, potassium tert-butoxide and dimethoxymagnesium, additionally organic bases, e.g. tertiary amines such as trimethylamine, triethylamine, triisopropylamine and N-methylpiperidine, pyridine, substituted pyridines such as collidine, lutidine and 4-dimethylaminopyridine, and bicyclic amines. Potassium carbonate, sodium hydroxide, triethylamine and sodium methoxide are particularly preferred.

In general, the bases are employed in catalytic amounts, but they can also be used in equimolar amounts, in excess or, if appropriate, as solvents.

When carrying out the process described above, the temperatures can be varied within a wide range. In general, the process is carried out at from 0 to 150° C., preferably from 20 to 130° C.

The process is customarily carried out at normal pressure. However, it is also possible to work at elevated or reduced pressure.

To carry out the process described above, in general from 1.0 to 3.0 mol, preferably 1.0 to 2.0 mol, of nucleophile Y—A—H and, if appropriate, from 1.0 to 3.0 mol, preferably 1.0 to 2.0 mol, of reaction auxiliary are employed per mole of XIIa. The reaction is carried out and worked up and the products are isolated by methods known per se.

The compounds of the formula XIIa can then be converted according to a process known per se into the dimethylaminomethylene derivatives of the formula XIIb (1. Chem. Ber. 1081 (65), 2. Chem. Ber. 3407 (64), 3. Synth. Communications 939 (82)).

On account of their C=C and C=N double bonds, the compounds I can be obtained as E/Z isomer mixtures which can be separated into the individual compounds in a customary manner, for example by crystallization or chromatography.

If isomer mixtures are obtained in the synthesis, in general, however, a separation is not absolutely necessary, as the individual isomers are partially converted into one another during preparation for use or in use (e.g. under the action of light, acid or base). Corresponding conversions can also take place after use, for example in the treatment of plants, in the treated plant or in the harmful fungus or animal pest to be controlled.

With regard to the C=N and C=C double bond of the substituents X, the E isomers of the compounds I are preferred with respect to their activity (configuration based on the $OCH_3$ or $CH_3$ group in relation to the $CO_2CH_3$ or $CONHCH_3$ group).

With regard to the —N=$CR^3$—CY=N double bonds, in general the cis-isomers of the compounds I (configuration based on the radical $R^3$ or Y in relation to the —$OCH_2$ or —$OR^4$ group) are preferred with respect to their activity.

In the definitions of the compounds I indicated at the outset, collective terms were used which are generally representative of the following groups:

halogen: fluorine, chlorine, bromine and iodine;
alkyl: straight-chain or branched alkyl groups having 1 to 4, 6 or 10 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
alkylamino: an amino group which carries a straight-chain or branched alkyl group having 1 to 6 carbon atoms as mentioned above;
dialkylamino: an amino group which carries two straight-chain or branched alkyl groups which are independent of one another and each have 1 to 6 carbon atoms as mentioned above;

alkylcarbonyl: straight-chain or branched alkyl groups having 1 to 10 carbon atoms, which are bonded to the structure via a carbonyl group (—CO—);

alkylsulfonyl: straight-chain or branched alkyl groups having 1 to 6 or 10 carbon atoms, which are bonded to the structure via a sulfonyl group (—SO$_2$—);

alkylsulfoxyl: straight-chain or branched alkyl groups having 1 to 6 carbon atoms, which are bonded to the structure via a sulfoxyl group (—S(=O)—);

alkylaminocarbonyl: Alkylamino groups having 1 to 6 carbon atoms as mentioned above, which are bonded to the structure via a carbonyl group (—CO—);

dialkylaminocarbonyl: dialkylamino groups each having 1 to 6 carbon atoms per alkyl radical as mentioned above, which are bonded to the structure via a carbonyl group (—CO—);

alkylaminothiocarbonyl: alkylamino groups having 1 to 6 carbon atoms as mentioned above, which are bonded to the structure via a thiocarbonyl group (—CS—);

dialkylaminothiocarbonyl: dialkylamino groups each having 1 to 6 carbon atoms per alkyl radical as mentioned above, which are bonded to the structure via a thiocarbonyl group (—CS—);

haloalkyl: straight-chain or branched alkyl groups having 1 to 6 carbon atoms, it being possible in these groups for the hydrogen atoms to be partially or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 or 6 carbon atoms as mentioned above, which are bonded to the structure via an oxygen atom (—O—), eg. $C_1$–$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkoxycarbonyl: straight-chain or branched alkyl groups having 1 to 6 carbon atoms, which are bonded to the structure via an oxycarbonyl group (—OC(=O)—);

haloalkoxy: straight-chain or branched alkyl groups having 1 to 6 carbon atoms, it being possible in these groups for the hydrogen atoms to be partially or completely replaced by halogen atoms as mentioned above, and these groups being bonded to the structure via an oxygen atom;

alkylthio: straight-chain or branched alkyl groups having 1 to 4 or 6 carbon atoms as mentioned above, which are bonded to the structure via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocyclic alkyl groups having 3 to 6 carbon ring members, eg. cyclopropyl, cyclobutyl, cyclopentyl and cyclohexyl;

alkenyl: straight-chain or branched alkenyl groups having 2 to 6 or 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkenyloxy: sraight-chain or branched alkenyl groups having 2 to 6 carbon atoms and a double bond in any desired position, which are bonded to the structure via an oxygen atom (—O—);

alkenylthio and alkenylamino: straight-chain or branched alkenyl groups having 2 to 6 carbon atoms and a double bond in any desired position, which (alkenylthio) are bonded to the structure via a sulfur atom or (alkenylamino) a nitrogen atom.

alkenylcarbonyl: straight-chain or branched alkenyl groups having 2 to 10 carbon atoms and a double bond in any desired position, which are bonded to the structure via a carbonyl group (—CO—);

alkynyl: straight-chain or branched akynyl groups having 2 to 10 carbon atoms and a triple bond in any desired position, eg. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynyloxy or alkynylthio and alkynylamino: straight-chain or branched alkynyl groups having 2 to 6 carbon atoms and a triple bond in any desired position, which (alkynyloxy) are bonded to the structure via an oxygen atom or (alkynylthio) via a sulfur atom or (alkynylamino) via a nitrogen atom.

alkynylcarbonyl: straight chain or branched alkynyl groups having 3 to 10 carbon atoms and a triple bond in any desired position, which are bonded to the structure via a carbonyl group (—CO—);

cycloalkenyl and cycloalkenyloxy, cycloalkenylthio and cycloalkenylamino: monocyclic alkenyl groups having 3 to 6 carbon ring members, which are bonded to the structure directly or (cycloalkenyloxy) via an oxygen atom or (cycloalkenylthio) a sulfur atom or (cycloalkenylamino) via a nitrogen atom, eg. cyclopropenyl, cyclobutenyl, cyclopentenyl or cyclohexenyl.

cycloalkoxy or cycloalkylthio and cycloalkylamino: monocyclic alkenyl groups having 3 to 6 carbon ring members, which (cycloalkoxy) are bonded to the structure via an oxygen atom or (cycloalkylthio) a sulfur atom or (cycloalkylamino) via a nitrogen atom, eg. cyclopropyl, cyclobutyl, cyclopentyl or cyclohexyl;

heterocyclyl or heterocyclyloxy, heterocyclylthio and heterocyclylamino: three- to six-membered, saturated or partially unsaturated mono- or polycyclic heterocycles, which contain 1 to 3 hetero atoms selected from a group consisting of oxygen, nitrogen and sulfur, and which are bonded to the structure directly or (heterocyclyloxy) via an oxygen atom or (heterocyclylthio) via a sulfur atom or (heterocyclylamino) via a nitrogen atom, such as, for example, 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydro-fur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl;

aryl or aryloxy, arylthio, arylcarbonyl and arylsulfonyl: aromatic mono- or polycyclic hydrocarbon radicals which are bonded to the structure directly or (aryloxy) via an oxygen atom (—O—) or g(arylthio) a sulfur atom (—S—), (arylcarbonyl) via a carbonyl group (—CO—) or (arylsulfonyl) via a sulfonyl group (—$SO_2$—), eg. phenyl, naphthyl and phenanthrenyl or phenoxy, naphthyloxy and phenanthrenyloxy and the corresponding carbonyl and sulfonyl radicals;

arylamino: aromatic mono- or polycyclic hydrocarbon radicals which are bonded to the structure via a nitrogen atom;

hetaryl or hetaryloxy, hetarylthio, hetarylcarbonyl and hetarylsulfonyl: aromatic mono- or polycyclic radicals which, beside carbon ring members, additionally can contain 1 to 4 nitrogen atoms or 1 to 3 nitrogen atoms and an oxygen atom or a sulfur atom or an oxygen atom or a sulfur atom and which are bonded to the structure directly or (hetaryloxy) via an oxygen atom (—O—) or (hetarylthio) a sulfur atom (—S—), (hetarylcarbonyl) via a carbonyl group (—CO—) or (hetarylsulfonyl) via a sulfonyl group ($SO_2$—), eg.

5-membered heteroaryl, comprising one to three nitrogen atoms: 5-membered ring heteroaryl groups which, beside carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl, comprising one to four nitrogen atoms or one to three nitrogen atoms and a sulfur or oxygen atom or an oxygen or a sulfur atom: 5-membered ring heteroaryl groups which, beside carbon atoms, can contain one to four nitrogen atoms or one to three nitrogen atoms and a sulfur or oxygen atom or an oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl, comprising one to three nitrogen atoms or a nitrogen atom and/or an oxygen or sulfur atom: 5-membered ring heteroaryl groups which, beside carbon atoms, can contain one to four nitrogen atoms or one to three nitrogen atoms and a sulfur or oxygen atom or an oxygen or a sulfur atom as ring members, and in which two adjacent carbon ring members or a nitrogen and an adjacent carbon ring member can be bridged by a buta-1,3-diene-1,4-diyl group;

5-membered heteroaryl bonded via nitrogen, comprising one to four nitrogen atoms, or benzo-fused 5-membered heteroaryl bonded via nitrogen, comprising one to three nitrogen atoms: 5-membered ring hetaryl groups which, beside carbon atoms, can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members;

6-membered heteroaryl. comprising one to three or one to four nitrogen atoms: 6-membered ring heteroaryl groups which, beside carbon atoms, can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl, comprising one to four nitrogen atoms: 6-membered ring heteroaryl groups in which two adjacent carbon ring members can be bridged by a buta-1,3-dien-1,4-diyl group, eg. quinoline, isoquinoline, quinazoline and quinoxaline, pyrido[3,2-d]thiazol-2-yl, or the corresponding oxy, thio, carbonyl or sulfonyl groups;

hetarylamino: aromatic mono- or polycyclic radicals which, beside carbon ring members, can additionally contain one to four nitrogen atoms or one to three nitrogen atoms and an oxygen or a sulfur atom and which are bonded to the structure via a nitrogen atom.

The term partially or completely halogenated is intended to express that in the groups characterized in this way the hydrogen atoms are partially or completely replaced by identical or different halogen atoms as mentioned above.

The term unsubstituted or substituted is intended to express that in the groups characterized in this way the hydrogen atoms are partially or completely replaced by identical or different groups, for example groups of the type which are mentioned under the collective terms detailed above.

With respect to their biological action, compounds of the formula I are preferred where $R^1$ is methyl and $R^2$ is hydrogen.

Compounds I are additionally preferred where $R^1$ is hydrogen and $R^2$ is methyl.

Compounds I are furthermore preferred where $R^1$ is trifluoromethyl and $R^2$ is hydrogen.

In addition, compounds I are preferred where $R^1$ is hydrogen and $R^2$ is trifluoromethyl.

Equally, compounds I are preferred where $R^1$ and $R^2$ are hydrogen.

Compounds I are particularly preferred where X is $C(CONHCH_3)=NOCH_3$.

Additionally, compounds I are preferred where X is $C(CO_2CH_3)=NOCH_3$.

Equally, compounds I are preferred where X is $C(CO_2CH_3)=CHOCH_3$.

In addition, compounds I are particularly preferred where X is $C(CO_2CH_3)=CHCH_3$.

Furthermore, compounds I are preferred where X is $N(CO_2CH_3)-OCH_3$.

Additionally, compounds I are particularly preferred where A is $-OCH_2-$.

Equally, compounds I are particularly preferred where A is $-C(R^3)=NOCH_2-$.

In additiion, compounds I are particularly preferred where A is

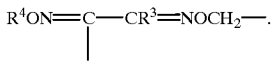

Furthermore, compounds I are preferred where A is $-O-$.

Equally, compounds I are particularly preferred where A is $-C(R^3)=N-O-$.

Furthermore, compounds I are particularly preferred where A is

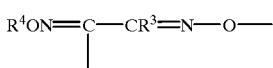

Additionally, compounds I are particularly preferred where $R^3$ is $C_1-C_4$-alkyl, in particular methyl.

Equally, particularly preferred compounds I are those where $R^3$ is trifluoromethyl.

In addition, compounds I are particularly preferred where $R^3$ is cyclopropyl.

Furthermore, compounds I are particularly preferred where $R^3$ is $C_1-C_4$-alkoxy, in particular methoxy.

In particular, compounds I are also preferred where Y is aryl, in particular unsubst. or subst. phenyl.

Additionally, compounds I are particularly preferred where Y is cycloalkyl, in particular cyclohexyl.

Additionally, compounds I are particularly preferred where Y is hetaryl, in particular unsubst. or subst. thienyl, isoxazolyl, pyrazolyl, pyridinyl and pyrimidinyl.

In particular, compounds I are also preferred where $R^4$ is $C_1-C_4$-alkyl, in particular methyl or ethyl.

Additionally, compounds I are particularly preferred where $R^4$ is $C_3-C_4$-alkenyl, in particular allyl.

Equally, particularly preferred compounds I are those where $R^4$ is $C_3-C_4$-alkynyl, in particular propargyl.

Furthermore, particularly preferred compounds I are those where $R^4$ is haloalkenyl, in particular trans-chloroallyl.

Table 1

Compounds of the general formula IA.1, where Y for a compound in each case corresponds to one line of Table B

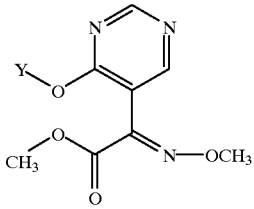

IA.1

Table 2

Compounds of the general formula IA.2 where Y for a compound in each case corresponds to one line of Table B

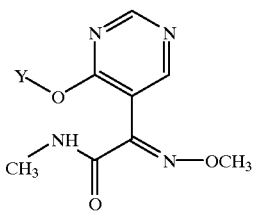

IA.2

Table 3

Compounds of the general formula IA.3 where Y for a compound in each case corresponds to one line of Table B

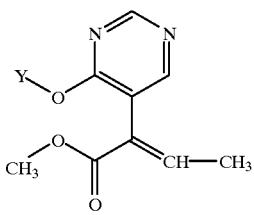

IA.3

Table 4

Compounds of the general formula IA.4 where Y for a compound in each case corresponds to one line of Table B

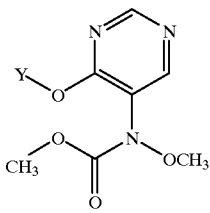

IA.4

Table 5

Compounds of the general formula IA.5 where Y for a compound in each case corresponds to one line of Table B

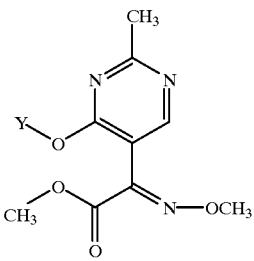

IA.5

Table 6

Compounds of the general formula IA.6 where Y for a compound in each case corresponds to one line of Table B

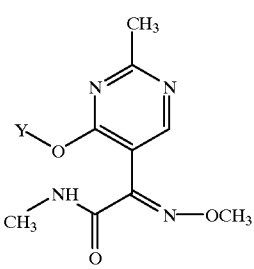

IA.6

Table 7

Compounds of the general formula IA.7 where Y for a compound in each case corresponds to one line of Table B

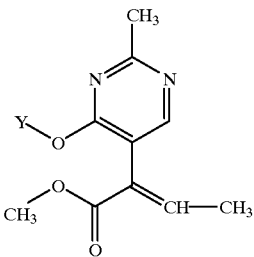

IA.7

Table 8

Compounds of the general formula IA.8 where Y for a compound in each case corresponds to one line of Table B

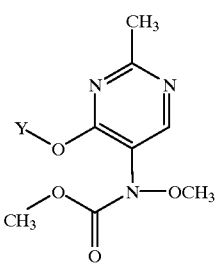

IA.8

Table 9

Compounds of the general formula IA.9 where Y for a compound in each case corresponds to one line of Table B

IA.9

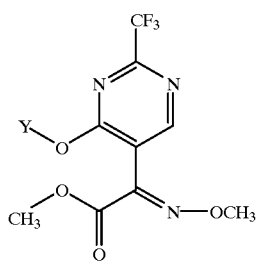

Table 10
Compounds of the general formula IA.10 where Y for a compound in each case corresponds to one line of Table B

IA.10

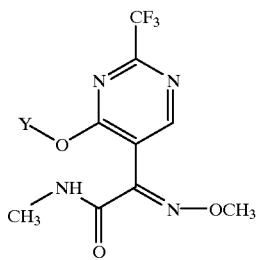

Table 11
Compounds of the general formula IA.11 where Y for a compound in each case corresponds to one line of Table B

IA.11

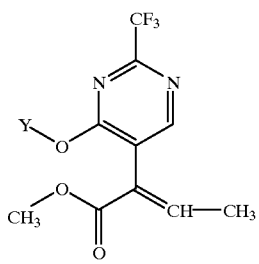

Table 12
Compounds of the general formula IA.12 where Y for a compound in each case corresponds to one line of Table B

IA.12

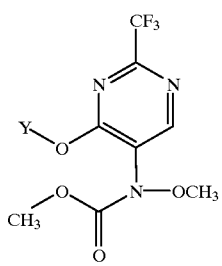

Table 13
Compounds of the general formula IA.13 where Y for a compound in each case corresponds to one line of Table B

IA.13

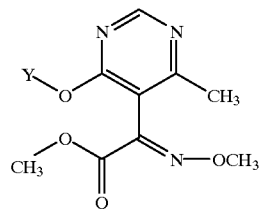

Table 14
Compounds of the general formula IA.14 where Y for a compound in each case corresponds to one line of Table B

IA.14

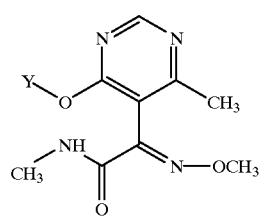

Table 15
Compounds of the general formula IA.15 where Y for a compound in each case corresponds to one line of Table B

IA.15

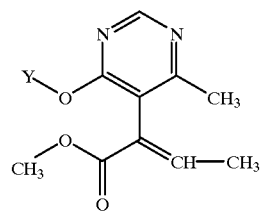

Table 16
Compounds of the general formula IA.16 where Y for a compound in each case corresponds to one line of Table B

IA.16

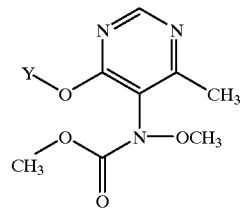

Table 17
Compounds of the general formula IA.17 where Y for a compound in each case corresponds to one line of Table A

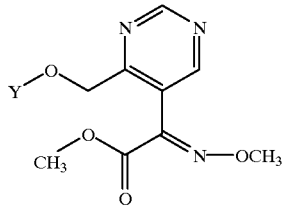

IA.17

Table 18

Compounds of the general formula IA.18 where Y for a compound in each case corresponds to one line of Table A

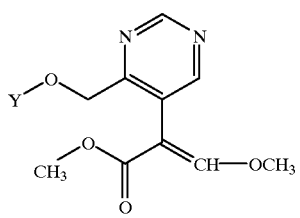

IA.18

Table 19

Compounds of the general formula IA.19 where Y for a compound in each case corresponds to one line of Table A

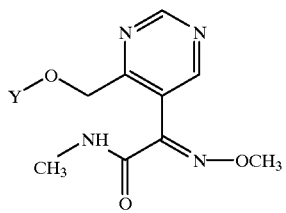

IA.19

Table 20

Compounds of the general formula IA.20 where Y for a compound in each case corresponds to one line of Table A

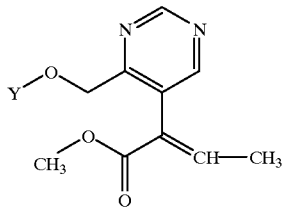

IA.20

Table 21

Compounds of the general formula IA.21 where Y for a compound in each case corresponds to one line of Table A

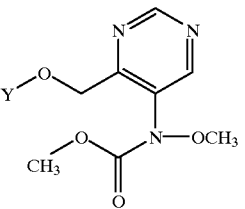

IA.21

Table 22

Compounds of the general formula IA.22 where Y for a compound in each case corresponds to one line of Table A

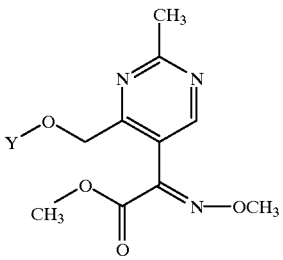

IA.22

Table 23

Compounds of the general formula IA.23 where Y for a compound in each case corresponds to one line of Table A

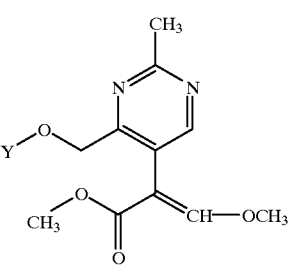

IA.23

Table 24

Compounds of the general formula IA.24 where Y for a compound in each case corresponds to one line of Table A

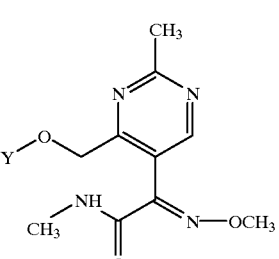

IA.24

Table 25

Compounds of the general formula IA.25 where Y for a compound in each case corresponds to one line of Table A

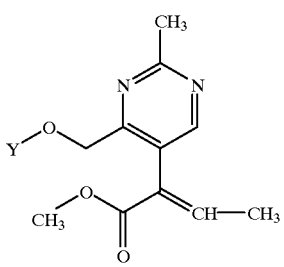
IA.25

Table 26
Compounds of the general formula IA.26 where Y for a compound in each case corresponds to one line of Table A

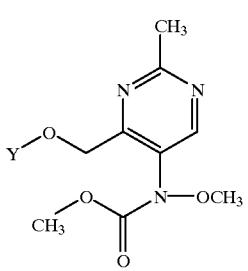
IA.26

Table 27
Compounds of the general formula IA.27 where Y for a compound in each case corresponds to one line of Table A

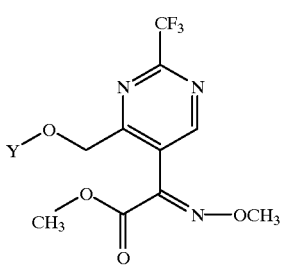
IA.27

Table 28
Compounds of the general formula IA.28 where Y for a compound in each case corresponds to one line of Table A

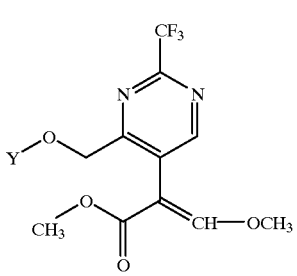
IA.28

Table 29
Compounds of the general formula IA.29 where Y for a compound in each case corresponds to one line of Table A

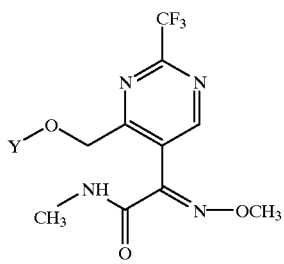
IA.29

Table 30
Compounds of the general formula IA.30 where Y for a compound in each case corresponds to one line of Table A

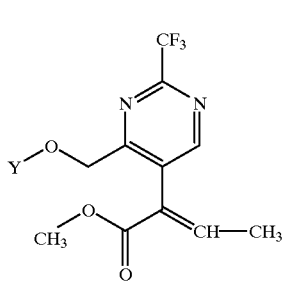
IA.30

Table 31
Compounds of the general formula IA.31 where Y for a compound in each case corresponds to one line of Table A

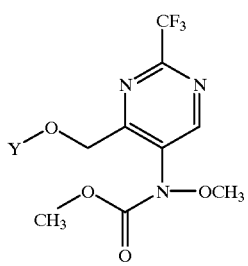
IA.31

Table 32
Compounds of the general formula IA.32 where Y for a compound in each case corresponds to one line of Table A

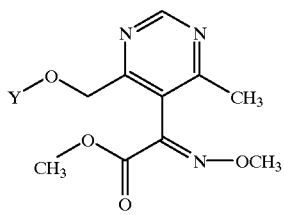
IA.32

Table 33
Compounds of the general formula IA.33 where Y for a compound in each case corresponds to one line of Table A

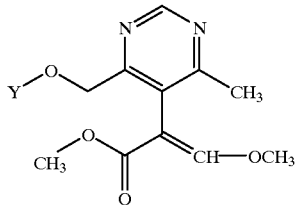

IA.33

Table 34
Compounds of the general formula IA.34 where Y for a compound in each case corresponds to one line of Table A

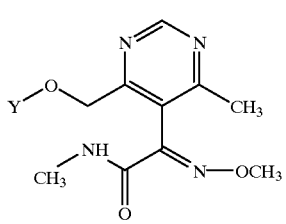

IA.34

Table 35
Compounds of the general formula IA.35 where Y for a compound in each case corresponds to one line of Table A

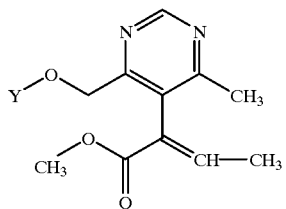

IA.35

Table 36
Compounds of the general formula IA.36 where Y for a compound in each case corresponds to one line of Table A

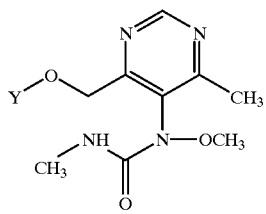

IA.36

Table 37
Compounds of the general formula IA.37 where Y for a compound in each case corresponds to one line of Table C

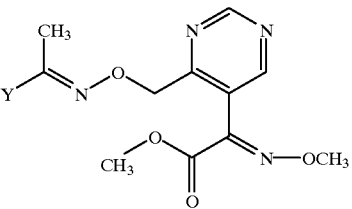

IA.37

Table 38
Compounds of the general formula IA.38 where Y for a compound in each case corresponds to one line of Table C

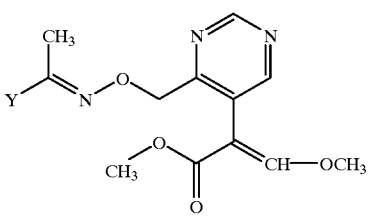

IA.38

Table 39
Compounds of the general formula IA.39 where Y for a compound in each case corresponds to one line of Table C

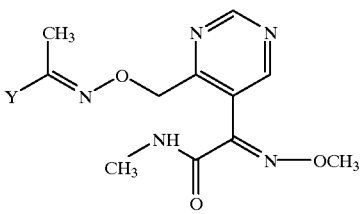

IA.39

Table 40
Compounds of the general formula IA.40 where Y for a compound in each case corresponds to one line of Table C

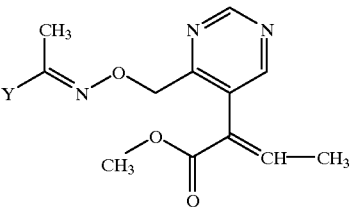

IA.40

Table 41
Compounds of the general formula IA.41 where Y for a compound in each case corresponds to one line of Table C

IA.41

Table 42
Compounds of the general formula IA.42 where Y for a compound in each case corresponds to one line of Table C

IA.42

Table 43
Compounds of the general formula IA.43 where Y for a compound in each case corresponds to one line of Table C

IA.43

Table 44
Compounds of the general formula IA.44 where Y for a compound in each case corresponds to one line of Table C

IA.44

Table 45
Compounds of the general formula IA.45 where Y for a compound in each case corresponds to one line of Table C

IA.45

Table 46
Compounds of the general formula IA.46 where Y for a compound in each case corresponds to one line of Table C

IA.46

Table 47
Compounds of the general formula IA.47 where Y for a compound in each case corresponds to one line of Table C

IA.47

Table 48
Compounds of the general formula IA.48 where Y for a compound in each case corresponds to one line of Table C

IA.48

Table 49
Compounds of the general formula IA.49 where Y for a compound in each case corresponds to one line of Table C

IA.49

Table 50
Compounds of the general formula IA.50 where Y for a compound in each case corresponds to one line of Table C

IA.50

Table 51
Compounds of the general formula IA.51 where Y for a compound in each case corresponds to one line of Table C

IA.51

Table 52
Compounds of the general formula IA.52 where Y for a compound in each case corresponds to one line of Table C

IA.52

Table 53
Compounds of the general formula IA.53 where Y for a compound in each case corresponds to one line of Table C

IA.53

Table 54
Compounds of the general formula IA.54 where Y for a compound in each case corresponds to one line of Table C

IA.54

Table 55
Compounds of the general formula IA.55 where Y for a compound in each case corresponds to one line of Table C

IA.55

Table 56
Compounds of the general formula IA.56 where Y for a compound in each case corresponds to one line of Table C

IA.56

Table 57
Compounds of the general formula IA.57 where Y and $R^4$ for a compound in each case correspond to one line of Table D

IA.57

Table 58
Compounds of the general formula IA.58 where Y and R⁴ for a compound in each case correspond to one line of Table D

IA.58

Table 59
Compounds of the general formula IA.59 where Y and R⁴ for a compound in each case correspond to one line of Table D

IA.59

Table 60
Compounds of the general formula IA.60 where Y and R⁴ for a compound in each case correspond to one line of Table D

IA.60

Table 61
Compounds of the general formula IA.61 where Y and R4 for a compound in each case correspond to one line of Table D

IA.61

Table 62
Compounds of the general formula IA.62 where Y for a compound in each case corresponds to one line of Table C

IA.62

Table 63
Compounds of the general formula IA.63 where Y for a compound in each case corresponds to one line of Table C

IA.63

Table 64
Compounds of the general formula IA.64 where Y for a compound in each case corresponds to one line of Table A

IA.64

Table 65
Compounds of the general formula IA.65 where Y for a compound in each case corresponds to one line of Table A

IA.65

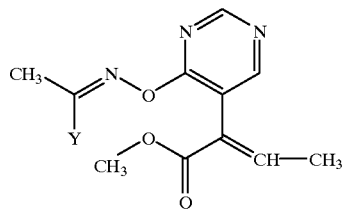

IA.69

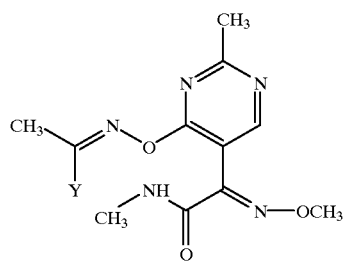

Table 66

Compounds of the general formula IA.66 where Y for a compound in each case corresponds to one line of Table C Table 70

Compounds of the general formula IA.70 where Y for a compound in each case corresponds to one line of Table C

IA.66

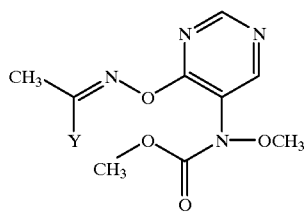

IA.70

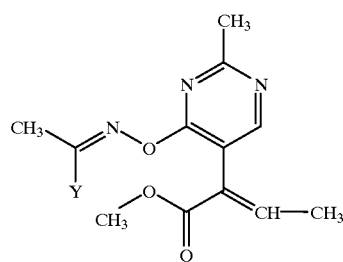

Table 67

Compounds of the general formula IA.67 where Y for a compound in each case corresponds to one line of Table C Table 71

Compounds of the general formula IA.71 where Y for a compound in each case corresponds to one line of Table C

IA.67

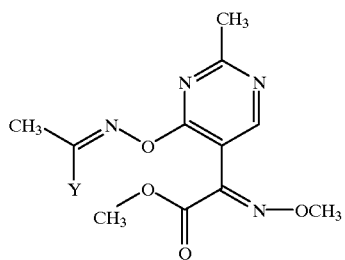

IA.71

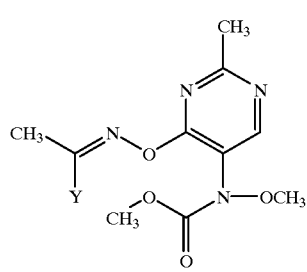

Table 68

Compounds of the general formula IA.68 where Y for a compound in each case corresponds to one line of Table C Table 72

Compounds of the general formula IA.72 where Y for a compound in each case corresponds to one line of Table C

IA.68

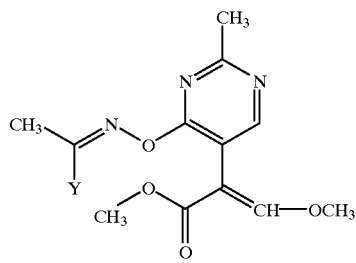

IA.72

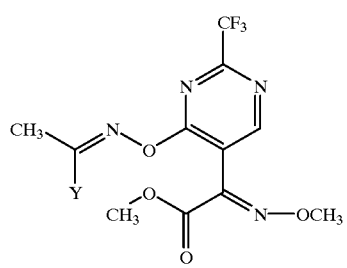

Table 69

Compounds of the general formula IA.69 where Y for a compound in each case corresponds to one line of Table C Table 73

Compounds of the general formula IA.73 where Y for a compound in each case corresponds to one line of Table C Table 74
Compounds of the general formula IA.74 where Y for a compound in each case corresponds to one line of Table C Table 75
Compounds of the general formula IA.75 where Y for a compound in each case corresponds to one line of Table C Table 76
Compounds of the general formula IA.76 where Y for a compound in each case corresponds to one line of Table C Table 77
Compounds of the general formula IA.77 where Y for a compound in each case corresponds to one line of Table C Table 78
Compounds of the general formula IA.78 where Y for a compound in each case corresponds to one line of Table C Table 79
Compounds of the general formula IA.79 where Y for a compound in each case corresponds to one line of Table C Table 80
Compounds of the general formula IA.80 where Y for a compound in each case corresponds to one line of Table C Table 81
Compounds of the general formula IA.81 where Y for a compound in each case corresponds to one line of Table C

IA.81

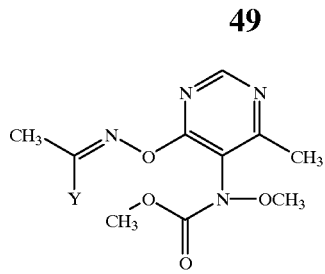

Table 82
Compounds of the general formula IA.82 where Y for a compound in each case corresponds to one line of Table D

IA.82

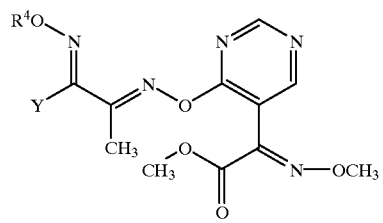

Table 83
Compounds of the general formula IA.83 where Y and $R^4$ for a compound in each case correspond to one line of Table D

IA.83

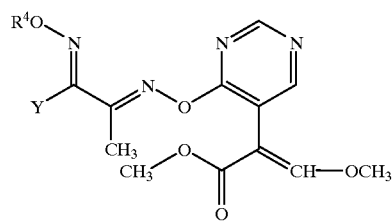

Table 84
Compounds of the general formula IA.84 where Y and $R^4$ for a compound in each case correspond to one line of Table D

IA.84

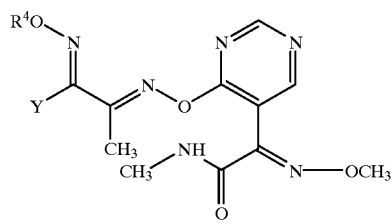

Table 85
Compounds of the general formula IA.85 where Y and $R^4$ for a compound in each case correspond to one line of Table D

IA.85

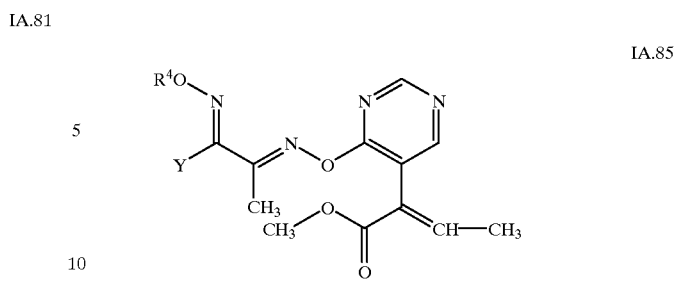

Table 86
Compounds of the general formula IA.86 where Y and $R^4$ for a compound in each case correspond to one line of Table D

IA.86

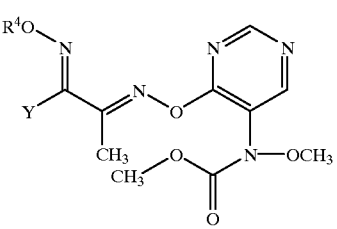

Table 87
Compounds of the general formula IA.87 where Y for a compound in each case corresponds to one line of Table E

IA.87

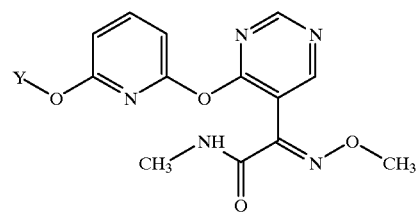

Table 88
Compounds of the general formula IA.88 where Y for a compound in each case corresponds to one line of Table E

IA.88

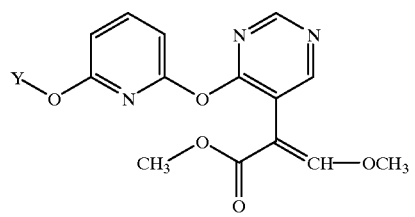

Table 89
Compounds of the general formula IA.89 where Y for a compound in each case corresponds to one line of Table E

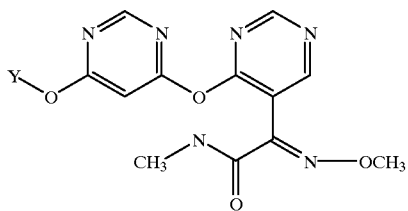

IA.89

Table 90

Compounds of the general formula IA.90 where Y for a compound in each case corresponds to one line of Table E

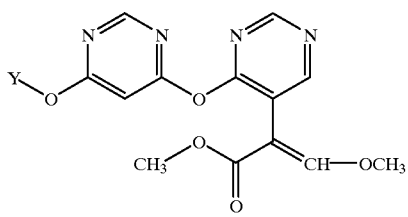

IA.90

Table 91

Compounds of the general formula IA.91 where the substitution pattern corresponds to the radicals of Table F

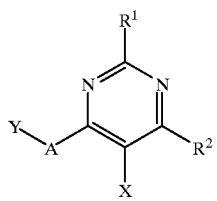

IA.91

TABLE A

| | |
|---|---|
| A.1 | C₆H₅ |
| A.2 | 2-F—C₆H₄ |
| A.3 | 3-F—C₆H₄ |
| A.4 | 4-F—C₆H₄ |
| A.5 | 2-Cl—C₆H₄ |
| A.6 | 3-Cl—C₆H₄ |
| A.7 | 4-Cl—C₆H₄ |
| A.8 | 2-CH₃—C₆H₄ |
| A.9 | 3-CH₃—C₆H₄ |
| A.10 | 3-CH₃—C₆H₄ |
| A.11 | 2,4-Cl₂—C₆H₃ |
| A.12 | 2,5-Cl₂—C₆H₃ |
| A.13 | 2-F—4-Cl—C₆H₃ |
| A.14 | 2-F—5-Cl—C₆H₃ |
| A.15 | 2-Cl—4-CH₃—C₆H₃ |
| A.16 | 2-CH₃—4-Cl—C₆H₃ |
| A.17 | 2-CH₃—5-Cl—C₆H₃ |
| A.18 | 2-Cl—5-CH₃—C₆H₃ |
| A.19 | 2,4-(CH₃)₂—C₆H₃ |
| A.20 | 2,5-(CH₃)₂—C₆H₃ |
| A.21 | 3,5-(CH₃)₂—C₆H₃ |
| A.22 | 2,3,5-(CH₃)₃—C₆H₂ |
| A.23 | 2,4,5-(CH₃)₃—C₆H₂ |
| A.24 | 2-CH₃—4-isopropyl—C₆H₃ |
| A.25 | 2-CH₃—4-tert-butyl—C₆H₃ |
| A.26 | 2-CH₃—4-phenyl—C₆H₃ |
| A.27 | 2-CH₃—5-phenyl—C₆H₃ |
| A.28 | 3-OH—C₆H₄ |

TABLE A-continued

| | |
|---|---|
| A.29 | 2-CH₃—4-OH—C₆H₃ |
| A.30 | 2-CH₃—5-OH—C₆H₃ |
| A.31 | 3-OCH₃—C₆H₄ |
| A.32 | 4-OCH₃—C₆H₄ |
| A.33 | 3-OEt—C₆H₄ |
| A.34 | 4-OEt—C₆H₄ |
| A.35 | 2-CH₃—4-OCH₃—C₆H₃ |
| A.36 | 2-CH₃—4-OC₂H₅—C₆H₃ |
| A.37 | 2-CH₃—4-O—n-propyl—C₆H₃ |
| A.38 | 2-CH₃—4-O—n-butyl—C₆H₃ |
| A.39 | 2-CH₃—4-O—phenyl—C₆H₃ |
| A.40 | 3-O—Phenyl—C₆H₄ |
| A.41 | 4-O—Phenyl—C₆H₄ |
| A.42 | 1-Naphthyl |
| A.43 | 2-Naphthyl |
| A.44 | 3-COCH₃—C₆H₄ |
| A.45 | 4-COCH₃—C₆H₄ |
| A.46 | 2-CH₃—4-OCH₃—C₆H₃ |
| A.47 | 2-CH₃—5-COCH₃—C₆H₃ |
| A.48 | 2-CH₃—4-CHO—C₆H₃ |
| A.49 | 2-CH₃—5-CHO—C₆H₃ |
| A.50 | 3-CHO—C₆H₄ |
| A.51 | 2-Cl—4-COCH₃—C₆H₃ |
| A.52 | 2,5-(CH₃)₂—4-COCH₃—C₆H₂ |
| A.53 | 2-CH₃—5-Cl—4-COCH₃—C₆H₂ |
| A.54 | 3-[C(CH₃)=NOH]—C₆H₄ |
| A.55 | 3-[C(CH₃)=NOCH₃]—C₆H₄ |
| A.56 | 3-[C(CH₃)=NOCH₂CH₃]—C₆H₄ |
| A.57 | 3-[C(CH₃)=NOCH₂CH₂CH₃]—C₆H₄ |
| A.58 | 3-[C(CH₃)=NOCH₂CH=CH₂]—C₆H₄ |
| A.59 | 3-[C(CH₃)=NOCH₂C≡CH]—C₆H₄ |
| A.60 | 2-CH₃—4-[C(CH₃)=NOCH₃]—C₆H₃ |
| A.61 | 2-CH₃—4-[C(CH₃)=NOCH₂CH₃]—C₆H₃ |
| A.62 | 2-CH₃—4-[C(CH₃)=NOCH₂CH₂CH₃]—C₆H₃ |
| A.63 | 2-CH₃—4-[C(CH₃)=NOCH₂CH=CH₂]—C₆H₃ |
| A.64 | 2-CH₃—4-[C(CH₃)=NOCH₂—C≡CH]—C₆H₃ |
| A.65 | 2,5-(CH₃)₂—4-[C(CH₃)=NOCH₃]—C₆H₂ |
| A.66 | 2,5-(CH₃)₂—4-[C(CH₃)=NOCH₂CH₃]—C₆H₂ |
| A.67 | 2,5-(CH₃)₂—4-[C(CH₃)=NOCH₂CH₂CH₃]—C₆H₂ |
| A.68 | 2,5-(CH₃)₂—4-[C(CH₃)=NOCH₂CH=CH₂]—C₆H₂ |
| A.69 | 2,5-(CH₃)₂—4-[C(CH₃)=NOCH₂—C≡CH]—C₆H₂ |
| A.70 | 2-CH₃—5-[C(CH₃)=NOCH₃]—C₆H₃ |
| A.71 | 2-CH₃—5-[C(CH₃)=NOCH₂CH₃]—C₆H₃ |
| A.72 | 2-CH₃—5-[C(CH₃)NOCH₂CH₂CH₃]—C₆H₅ |
| A.73 | 2-CH₃—5-[C(CH₃)=NOCH₂—CH=CH₂]—C₆H₃ |
| A.74 | 2-CH₃—5-[C(CH₃)=NOCH₂C≡CH]—C₆H₃ |
| A.75 | 2-CH₃—5-Cl—4-[C(CH₃)=NOCH₃]—C₆H₂ |
| A.76 | 2-CH₃—4-[C(CH₂CH₃)=NOCH₃]—C₆H₃ |
| A.77 | 2-CH₃—4-[C(CH₂CH₃)=NOCH₂CH₃]—C₆H₃ |
| A.78 | 2-Pyridyl |
| A.79 | 6-Methyl-2-pyridyl |
| A.80 | 6-n-Propyl-2-pyridyl |
| A.81 | 6-n-Butyl-2-pyridyl |
| A.82 | 6-tert-Butyl-2-pyridyl |
| A.83 | 6-n-Pentyl-2-pyridyl |
| A.84 | 6-n-Hexyl-2-pyridyl |
| A.85 | 6-Phenyl-2-pyridyl |
| A.86 | 6-Benzyl-2-pyridyl |
| A.87 | 6-Trifluoromethyl-2-pyridyl |
| A.88 | 6-Methoxy-2-pyridyl |
| A.89 | 6-Chloro-2-pyridyl |
| A.90 | 3,6-Dimethyl-2-pyridyl |
| A.91 | 3,6-Diethyl-2-pyridyl |
| A.92 | 4,6-Dimethyl-2-pyridyl |
| A.93 | 5,6-Dimethyl-2-pyridyl |
| A.94 | 4-Phenyl-6-methyl-2-pyridyl |
| A.95 | 4,6-Diphenyl-2-pyridyl |
| A.96 | 3,4-Dichloro-6-methyl-2-pyridyl |
| A.97 | 3,4,5-Trichloro-6-phenyl-2-pyridyl |
| A.98 | 4-Trifluoromethyl-6-methyl-2-pyridyl |
| A.99 | 3-Acetyl-4,6-dimethyl-2-pyridyl |
| A.100 | 3-Cyano-6-methyl-2-pyridyl |
| A.101 | 3-Cyano-6-ethyl-2-pyridyl |
| A.102 | 3-Cyano-6-n-propyl-2-pyridyl |
| A.103 | 3-Cyano-6-isopropyl-2-pyridyl |
| A.104 | 3-Cyano-6-cyclopropyl-2-pyridyl |
| A.105 | 3-Cyano-6-n-butyl-2-pyridyl |
| A.106 | 3-Cyano-6-tert-butyl-2-pyridyl |
| A.107 | 3-Cyano-6-cyclohexyl-2-pyridyl |

TABLE A-continued

| | |
|---|---|
| A.108 | 3-Cyano-6-phenyl-2-pyridyl |
| A.109 | 3-Methoxycarbonyl-6-isopropyl-2-pyridyl |
| A.110 | 3-Ethyloxycarbonyl-6-isopropyl-2-pyridyl |
| A.111 | 3-Cyano-4,6-dimethyl-2-pyridyl |
| A.112 | 3,5,6-Trichloro-2-pyridyl |
| A.113 | 5-Trifluoromethyl-2-pyridyl |
| A.114 | 3-Chloro-5-trifluoromethyl-2-pyridyl |
| A.115 | 6-Cyclopropyl-2-pyridyl |
| A.116 | 6-Bromo-2-pyridyl |
| A.117 | 4-Trifluoromethyl-2-pyridyl |
| A.118 | 4-Trifluoromethyl-5-chloro-2-pyridyl |
| A.119 | 4-tert-Butyl-2-pyridyl |
| A.120 | 3,6-Bis(trifluoromethyl)-2-pyridyl |
| A.121 | 5-Trifluoromethyl-2-pyridyl |
| A.122 | 3-Fluoro-2-pyridyl |
| A.123 | 3-Chloro-2-pyridyl |
| A.124 | 4-Bromo-2-pyridyl |
| A.125 | 5-Methyl-2-pyridyl |
| A.126 | 3-Fluoro-5-trifluoromethyl-2-pyridyl |
| A.127 | 3,6-Dichloro-5-trifluoromethyl-2-pyridyl |
| A.128 | 6-Chloro-4-cyano-2-pyridyl |
| A.129 | 3-Cyano-5-nitro-2-pyridyl |
| A.130 | 4,6-Difluoro-2-pyridyl |
| A.131 | 3,5-Dichloro-6-fluoro-2-pyridyl |
| A.132 | 6-Methoxy-3-nitro-2-pyridyl |
| A.133 | 4-Cyano-6-fluoro-2-pyridyl |
| A.134 | 4-Cyano-3,5,6,-trifluoro-2-pyridyl |
| A.135 | 6-Chloro-5-nitro-2-pyridyl |
| A.136 | 4,6-Dicyano-2-pyridyl |
| A.137 | 5-Trichloromethyl-2-pyridyl |
| A.138 | 5-Cyano-2-pyridyl |
| A.139 | 5-Bromo-4-trifluoromethyl-2-pyridyl |
| A.140 | 3-Nitro-5-trifluoromethyl-2-pyridyl |
| A.141 | 5-Formamido-2-pyridyl |
| A.142 | 5-Amino-2-pyridyl |
| A.143 | 5-Nitro-2-pyridyl |
| A.144 | 4-Methyl-5-nitro-2-pyridyl |
| A.145 | 5-Difluoromethyl-2-pyridyl |
| A.146 | 5-Fluoromethyl-2-pyridyl |
| A.147 | 5-Methoxycarbonyl-2-pyridyl |
| A.148 | 5-Chloro-6-methoxy-2-pyridyl |
| A.149 | 5,6-Dichloro-2-pyridyl |
| A.150 | 6-Bromo-5-chloro-2-pyridyl |
| A.151 | 5-Chloro-6-acetoxy-2-pyridyl |
| A.152 | 5-Bromo-6-fluoro-2-pyridyl |
| A.153 | 5-Bromo-6-cyano-2-pyridyl |
| A.154 | 5-Bromo-6-hydroxy-2-pyridyl |
| A.155 | 5-Bromo-6-methoxy-2-pyridyl |
| A.156 | 5,6-Dibromo-2-pyridyl |
| A.157 | 6-Phenoxy-2-pyridyl |
| A.158 | 4-Phenyl-2-pyridyl |
| A.159 | 4-Phenoxy-2-pyridyl |
| A.160 | 6-Hydroxy-2-pyridyl |
| A.161 | 6-Ethoxy-2-pyridyl |
| A.162 | 6-Benzyloxy-2-pyridyl |
| A.163 | 4-Benzyloxy-2-pyridyl |
| A.164 | 4,6-Bis(trifluoromethyl)-2-pyridyl |
| A.165 | 6-Formyl-2-pyridyl |
| A.166 | 6-Amino-2-pyridyl |
| A.167 | 4-Amino-2-pyridyl |
| A.168 | 4-Carboxy-2-pyridyl |
| A.169 | 3-Bromo-5-trifluoromethyl-2-pyridyl |
| A.170 | 6-Methyl-3-nitro-2-pyridyl |
| A.171 | 3-Nitro-2-pyridyl |
| A.172 | 3-Fluoro-5-trifluoromethyl-2-pyridyl |
| A.173 | 3-Pyridyl |
| A.174 | 2-Fluoro-3-pyridyl |
| A.175 | 4-Trifluoromethyl-3-pyridyl |
| A.176 | 5-Methyl-3-pyridyl |
| A.177 | 6-Methoxy-3-pyridyl |
| A.178 | 4-Cyano-2,5,6,-trifluoro-3-pyridyl |
| A.179 | 4-Pyridyl |
| A.180 | 2-Chloro-4-pyridyl |
| A.181 | 3-Trifluoromethyl-4-pyridyl |
| A.182 | 2-Chloro-6-fluoro-4-pyridyl |
| A.183 | 2,3,5,6-Tetrafluoro-4-pyridyl |
| A.184 | 2-Pyrimidinyl |
| A.185 | 4,6-Dimethyl-2-pyrimidinyl |
| A.186 | 4-Trifluoromethyl-2-pyrimidinyl |
| A.187 | 4,5,6-Trimethyl-2-pyrimidinyl |
| A.188 | 4-Benzyl-6-methyl-2-pyrimidinyl |
| A.189 | 4-Methyl-6-phenyl-2-pyrimidinyl |
| A.190 | 4,6-Dimethyl-5-chloro-pyrimidinyl |
| A.191 | 4-Fluoro-2-pyrimidinyl |
| A.192 | 5-Methyl-2-pyrimidinyl |
| A.193 | 4,6-Difluoro-2-pyrimidinyl |
| A.194 | 4-Methyl-2-pyrimidinyl |
| A.195 | 4-Pyrimidinyl |
| A.196 | 2,6-Dimethyl-4-pyrimidinyl |
| A.197 | 2,6-Bis(trifluoromethyl)-4-pyrimidinyl |
| A.198 | 2-Chloromethyl-6-methyl-4-pyrimidinyl |
| A.199 | 2-Methyl-6-chloromethyl-4-pyrimidinyl |
| A.200 | 2-iso-Propyl-6-methyl-4-pyrimidinyl |
| A.201 | 2-iso-Propyl-6-chloromethyl-4-pyrimidinyl |
| A.202 | 2-cyclo-Propyl-6-chloromethyl-4-pyrimidinyl |
| A.203 | 2-cyclo-Propyl-6-methyl-4-pyrimidinyl |
| A.204 | 2-Methyl-6-methoxymethyl-4-pyrimidinyl |
| A.205 | 2-iso-Propyl-6-methoxymethyl-4-pyrimidinyl |
| A.206 | 2-Phenyl-4-pyrimidinyl |
| A.207 | 2,5-Dimethyl-4-pyrimidinyl |
| A.208 | 2-Methylthio-6-trifluoromethyl-4-pyrimidinyl |
| A.209 | 2-Methylthio-5-chloro-6-trifluoromethyl-4-pyrimidinyl |
| A.210 | 2-Methylthio-5-n-octyl-6-methyl-4-pyrimidinyl |
| A.211 | 2-Methyl-6-trifluoromethyl-4-pyrimidinyl |
| A.212 | 2-n-Propyl-6-trifluoromethyl-4-pyrimidinyl |
| A.213 | 2-iso-Propyl-6-trifluoromethyl-4-pyrimidinyl |
| A.214 | 2-n-Propyl-6-methyl-4-pyrimidinyl |
| A.215 | 2-tert-Butyl-6-trifluoromethyl-4-pyrimidinyl |
| A.216 | 2-Methyl-5-chloro-6-trifluoromethyl-4-pyrimidinyl |
| A.217 | 2-n-Propyl-5-chloro-6-trifluoromethyl-4-pyrimidinyl |
| A.218 | 2-iso-Propyl-5-chloro-6-trifluoromethyl-4-pyrimidinyl |
| A.219 | 2-tert-Butyl-5-chloro-6-trifluoromethyl-4-pyrimidinyl |
| A.220 | 2-Chloro-4-pyrimidinyl |
| A.221 | 5-Methoxy-4-pyrimidinyl |
| A.222 | 6-Trifluoromethyl-4-pyrimidinyl |
| A.223 | 2-Chloro-6-trichloromethyl-4-pyrimidinyl |
| A.224 | 2,6-Dichloro-4-pyrimidinyl |
| A.225 | 2-Phenyl-6-trifluoromethyl-4-pyrimidinyl |
| A.226 | 2-Methylthio-6-difluoromethoxy-4-pyrimidyl |
| A.227 | 2-Ethyl-6-trifluoromethyl-4-pyrimidinyl |
| A.228 | 2-Cyclo-propyl-6-trifluoromethyl-4-pyrimidinyl |
| A.229 | 2-Phenyl-6-trifluoromethyl-4-pyrimidinyl |
| A.230 | 2-Methylthio-5-chloro-6-methoxy-4-pyrimidinyl |
| A.231 | 2-Dimethylamino-5-n-butyl-6-methyl-4-pyrimidinyl |
| A.232 | 2-Dimethylamino-5-nitro-6-methyl-4-pyrimidinyl |
| A.233 | 2-Quinolyl |
| A.234 | 3-Methyl-2-quinolyl |
| A.235 | 4-Methyl-2-quinolyl |
| A.236 | 4-Ethyl-2-quinolyl |
| A.237 | 4-Phenyl-2-quinolyl |
| A.238 | 6-Methyl-2-quinolyl |
| A.239 | 6-Chloro-2-quinolyl |
| A.240 | 8-Methyl-2-quinolyl |
| A.241 | 8-Chloro-2-quinolyl |
| A.242 | 4-Ethoxycarbonyl-2-quinolyl |
| A.243 | 3,4-Dimethyl-2-quinolyl |
| A.244 | 4-Methyl-8-methoxy-2-quinolyl |
| A.245 | 4-Phenyl-8-ethoxy-2-quinolyl |
| A.246 | 4-Methyl-8-chloro-2-quinolyl |
| A.247 | 4-Methyl-8-fluoro-2-quinolyl |
| A.248 | 4-Quinolyl |
| A.249 | 2-Methyl-4-quinolyl |
| A.250 | 2-Trichloromethyl-4-quinolyl |
| A.251 | 2-Trifluoromethyl-2-quinolyl |
| A.252 | 2-iso-Propyl-4-quinolyl |
| A.253 | 2-n-Pentyl-4-quinolyl |
| A.254 | 2-Phenyl-4-quinolyl |
| A.255 | 2-Methoxycarbonyl-4-quinolyl |
| A.256 | 2,6-Dimethyl-4-quinolyl |
| A.257 | 2-Methyl-6-chloro-4-quinolyl |
| A.258 | 8-Quinolyl |
| A.259 | 2-Methyl-8-quinolyl |
| A.260 | 5,7-Dichloro-8-quinolyl |
| A.261 | 2-Pyrazinyl |
| A.262 | 6-Chloro-2-pyrazinyl |
| A.263 | 5-Methyl-2-pyrazinyl |
| A.264 | 3-Pyridazinyl |
| A.265 | 5-Chloro-3-pyridazinyl |

TABLE A-continued

| | |
|---|---|
| A.266 | 2-Thienyl |
| A.267 | 3-Thienyl |
| A.268 | 4-Chloro-3-thienyl |
| A.269 | 2-Chloro-3-thienyl |
| A.270 | 5-Chloro-3-thienyl |
| A.271 | 4-Chloro-2-thienyl |
| A.272 | 5-Chloro-2-thienyl |
| A.273 | 2-Quinoxalinyl |
| A.274 | 3-Methyl-2-quinoxalinyl |
| A.275 | 7,8-Dimethyl-2-quinoxalinyl |
| A.276 | 7,8-Dichloro-2-quinoxalinyl |
| A.277 | 7-Methyl-2-quinoxalinyl |
| A.278 | 8-Methyl-2-quinoxalinyl |
| A.279 | 7-Methoxy-2-quinoxalinyl |
| A.280 | 3-Phenyl-5-isoxazolyl |
| A.281 | 2-Benzoxazolyl |
| A.282 | 2-Benzothiazolyl |
| A.283 | 1-Phenyl-pyrazol-4-yl |
| A.284 | 2-n-Propyl-6-methyl-4-pyrimidinyl |
| A.285 | 2-n-Propyl-6-methyl-4-pyrimidinyl |
| A.286 | 2-Cyclopentyl-6-trifluoromethyl-4-pyrimidyl |
| A.287 | 2-Cyclohexyl-6-trifluoromethyl-4-pyrimidyl |
| A.288 | 2-Cyclohexyl-5-chloro-6-methyl-4-pyrimidyl |
| A.289 | 2-n-Propyl-5-chloro-6-methyl-4-pyrimidyl |
| A.290 | Pyrazol-1-yl |
| A.291 | 4-Chloropyrazol-1-yl |

TABLE B

| | |
|---|---|
| B.1 | $C_6H_5$ |
| B.2 | 2-F—$C_6H_4$ |
| B.3 | 3-F—$C_6H_4$ |
| B.4 | 4-F—$C_6H_4$ |
| B.5 | 2-Cl—$C_6H_4$ |
| B.6 | 3-Cl—$C_6H_4$ |
| B.7 | 4-Cl—$C_6H_4$ |
| B.8 | 2-$CH_3$—$C_6H_4$ |
| B.9 | 3-$CH_3$—$C_6H_4$ |
| B.10 | 3-$CH_3$—$C_6H_4$ |
| B.11 | 2,4-$Cl_2$—$C_6H_3$ |
| B.12 | 2,5-$Cl_2$—$C_6H_3$ |
| B.13 | 2-F—4-Cl—$C_6H_3$ |
| B.14 | 2-F—5-Cl—$C_6H_3$ |
| B.15 | 2-Cl—4-$CH_3$—$C_6H_3$ |
| B.16 | 2-$CH_3$—4-Cl—$C_6H_3$ |
| B.17 | 2-$CH_3$—5-Cl—$C_6H_3$ |
| B.18 | 2-Cl—5-$CH_3$—$C_6H_3$ |
| B.19 | 2-4-($CH_3$)$_2$—$C_6H_3$ |
| B.20 | 2-5-($CH_3$)$_2$—$C_6H_3$ |
| B.21 | 3,5-($CH_3$)$_2$—$C_6H_3$ |
| B.22 | 2,3,5-($CH_3$)$_3$—$C_6H_2$ |
| B.23 | 2,4,5-($CH_3$)$_3$—$C_6H_2$ |
| B.24 | 2-$CH_3$—4-isopropyl—$C_6H_3$ |
| B.25 | 2-$CH_3$—4-tert-butyl—$C_6H_3$ |
| B.26 | 2-$CH_3$—4-phenyl—$C_6H_3$ |
| B.27 | 2-$CH_3$—5-phenyl—$C_6H_3$ |
| B.28 | 3-OH—$C_6H_4$ |
| B.29 | 2-$CH_3$—4-OH—$C_6H_3$ |
| B.30 | 2-$CH_3$—5-OH—$C_6H_3$ |
| B.31 | 3-$OCH_3$—$C_6H_4$ |
| B.32 | 4-$OCH_3$—$C_6H_4$ |
| B.33 | 3-OEt—$C_6H_4$ |
| B.34 | 4-OEt—$C_6H_4$ |
| B.35 | 2-$CH_3$—4-$OCH_3$—$C_6H_3$ |
| B.36 | 2-$CH_3$—4-$OC_2H_5$—$C_6H_3$ |
| B.37 | 2-$CH_3$—4-O—n-propyl—$C_6H_3$ |
| B.38 | 2-$CH_3$—4-O—n-butyl—$C_6H_3$ |
| B.39 | 2-$CH_3$—4-O—phenyl—$C_6H_3$ |
| B.40 | 3-O—phenyl—$C_6H_4$ |
| B.41 | 4-O—phenyl—$C_6H_4$ |
| B.42 | 1-Naphthyl |
| B.43 | 2-Naphthyl |
| B.44 | 3-$COCH_3$—$C_6H_4$ |
| B.45 | 4-$COCH_3$—$C_6H_4$ |
| B.46 | 2-$CH_3$-4-$OCH_3$—$C_6H_3$ |
| B.47 | 2-$CH_3$-5-$COCH_3$—$C_6H_3$ |

TABLE B-continued

| | |
|---|---|
| B.48 | 2-$CH_3$-4-CHO—$C_6H_3$ |
| B.49 | 2-$CH_3$-5-CHO—$C_6H_3$ |
| B.50 | 3-CHO—$C_6H_4$ |
| B.51 | 2-Cl—4-$COCH_3$—$C_6H_3$ |
| B.52 | 2,5-($CH_3$)$_2$-4-$COCH_3$—$C_6H_2$ |
| B.53 | 2-$CH_3$-5-Cl—4-$COCH_3$—$C_6H_2$ |
| B.54 | 3-(2-F—$OC_6H_4$)—$C_6H_4$ |
| B.55 | 3-(2-$CH_3$—$OC_6H_4$)—$C_6H_4$ |
| B.56 | 3-(2-Cl—$OC_6H_4$)—$C_6H_4$ |
| B.57 | 3-(2-CN—$OC_6H_4$)—$C_6H_4$ |
| B.58 | 3-(2-$CO_2CH_3$—$OC_6H_4$)—$C_6H_4$ |
| B.59 | 3-(2,4-$F_2$—$OC_6H_3$)—$C_6H_4$ |
| B.60 | 3-(2,6-$F_2$—$OC_6H_3$)—$C_6H_4$ |
| B.61 | 3-(2,5-$F_2$—$OC_6H_3$)—$C_6H_4$ |
| B.62 | 3-(2,6-$Cl_2$—$OC_6H_3$)—$C_6H_4$ |
| B.63 | 3-(2,4-$Cl_2$—$OC_6H_3$)—$C_6H_4$ |
| B.64 | 3-[2,4-($CH_3$)$_2$—$OC_6H_3$]—$C_6H_4$ |
| B.65 | 3-[2,6-($CH_3$)$_2$—$OC_6H_3$]—$C_6H_4$ |
| B.66 | 3-(3-F—$OC_6H_4$)—$C_6H_4$ |
| B.67 | 3-(3-Cl—$OC_6H_4$)—$C_6H_4$ |
| B.68 | 3-(3-$CH_3$—$OC_6H_4$)—$C_6H_4$ |
| B.69 | 3-(4-F—$OC_6H_4$)—$C_6H_4$ |
| B.70 | 3-(4-Cl—$OC_6H_4$)—$C_6H_4$ |
| B.71 | 3-(4-$CH_3$—$OC_6H_4$)—$C_6H_4$ |
| B.72 | 3-(3-iso-Propyl—$OC_6H_4$)—$C_6H_4$ |
| B.73 | 3-(3-tert-Butyl—$OC_6H_4$)—$C_6H_4$ |
| B.74 | 3-(4-Isopropyl—$OC_6H_4$)—$C_6H_4$ |
| B.75 | 3-(4-tert-Butyl—$OC_6H_4$)—$C_6H_4$ |
| B.76 | 3-Fluoropyridin-2-yl |
| B.77 | 3-Chloropyridin-2-yl |
| B.78 | 3-Bromopyridin-2-yl |
| B.79 | 3-Methylpyridin-2-yl |
| B.80 | 3-Trifluoromethylpyridin-2-yl |
| B.81 | 3-Methoxypyridin-2-yl |
| B.82 | 4-Fluoropyridin-2-yl |
| B.83 | 4-Chloropyridin-2-yl |
| B.84 | 4-Bromopyridin-2-yl |
| B.85 | 4-Methylpyridin-2-yl |
| B.86 | 4-Trifluoromethylpyridin-2-yl |
| B.87 | 4-Methoxypyridin-2-yl |
| B.88 | 5-Fluoropyridin-2-yl |
| B.89 | 5-Chloropyridin-2-yl |
| B.90 | 5-Bromopyridin-2-yl |
| B.91 | 5-Methylpyridin-2-yl |
| B.92 | 5-Methoxypyridin-2-yl |
| B.93 | 6-Fluoropyridin-2-yl |
| B.94 | 6-Chloropyridin-2-yl |
| B.95 | 6-Bromopyridin-2-yl |
| B.96 | 6-Methylpyridin-2-yl |
| B.97 | 6-Trifluoromethylpyridin-2-yl |
| B.98 | 6-Methoxypyridin-2-yl |
| B.99 | 2-Fluoropyridin-3-yl |
| B.100 | 2-Chloropyridin-3-yl |
| B.101 | 2-Bromopyridin-3-yl |
| B.102 | 2-Methylpyridin-3-yl |
| B.103 | 2-Trifluoromethylpyridin-3-yl |
| B.104 | 3-Methoxypyridin-3-yl |
| B.105 | 4-Fluoropyridin-3-yl |
| B.106 | 4-Chloropyridin-3-yl |
| B.107 | 4-Bromopyridin-3-yl |
| B.108 | 4-Methylpyridin-3-yl |
| B.109 | 4-Trifluoromethylpyridin-3-yl |
| B.110 | 4-Methoxypyridin-3-yl |
| B.111 | 5-Fluoropyridin-3-yl |
| B.112 | 5-Chloropyridin-3-yl |
| B.113 | 5-Bromopyridin-3-yl |
| B.114 | 5-Methylpyridin-3-yl |
| B.115 | 5-Trifluoromethylpyridin-3-yl |
| B.116 | 5-Methoxypyridin-3-yl |
| B.117 | 6-Fluoropyridin-3-yl |
| B.118 | Pyridin-2-yl |
| B.119 | Pyridin-3-yl |
| B.120 | Pyridin-4-yl |
| B.121 | 6-Chloropyridin-3-yl |
| B.122 | 6-Bromopyridin-3-yl |
| B.123 | 6-Methylpyridin-3-yl |
| B.124 | 6-Trifluoromethylpyridin-3-yl |
| B.125 | 6-Methoxypyridin-3-yl |
| B.126 | 2-Fluoropyridin-4-yl |

TABLE B-continued

| | |
|---|---|
| B.127 | 2-Chloropyridin-4-yl |
| B.128 | 2-Bromopyridin-4-yl |
| B.129 | 2-Methylpyridin-4-yl |
| B.130 | 2-Trifluoromethylpyridin-4-yl |
| B.131 | 2-Methoxypyridin-4-yl |
| B.132 | 3-Fluoropyridin-4-yl |
| B.133 | 3-Chloropyridin-4-yl |
| B.134 | 3-Bromopyridin-4-yl |
| B.135 | 3-Methylpyridin-4-yl |
| B.136 | 3-Trifluoromethylpyridin-4-yl |
| B.137 | 3-Methoxypyridin-4-yl |
| B.138 | 4-Fluoropyrimidin-2-yl |
| B.139 | 4-Chloropyrimidin-2-yl |
| B.140 | 4-Bromopyrimidin-2-yl |
| B.141 | 4-Methylpyrimidin-2-yl |
| B.142 | 4-Trifluoromethylpyrimidin-2-yl |
| B.143 | 4-Methoxypyrimidin-2-yl |
| B.144 | 5-Fluoropyrimidin-2-yl |
| B.145 | 5-Chloropyrimidin-2-yl |
| B.146 | 5-Bromopyrimidin-2-yl |
| B.147 | 5-Methylpyrimidin-2-yl |
| B.148 | 5-Trifluoromethylpyrimidin-2-yl |
| B.149 | 5-Methoxypyrimidin-2-yl |
| B.150 | 2-Fluoropyrimidin-4-yl |
| B.151 | 2-Chloropyrimidin-4-yl |
| B.152 | 2-Bromopyrimidin-4-yl |
| B.153 | 2-Methylpyrimidin-4-yl |
| B.154 | 2-Trifluoromethylpyrimidin-4-yl |
| B.155 | 2-Methoxypyrimidin-4-yl |
| B.156 | 5-Fluoropyrimidin-4-yl |
| B.157 | 5-Chloropyrimidin-4-yl |
| B.158 | 5-Bromopyrimidin-4-yl |
| B.159 | 5-Methoxypyrimidin-4-yl |
| B.160 | 5-Trifluoromethylpyrimidin-4-yl |
| B.161 | 5-Methoxypyrimidin-4-yl |
| B.162 | 6-Fluoropyrimidin-4-yl |
| B.163 | 6-Chloropyrimidin-4-yl |
| B.164 | 6-Bromopyrimidin-4-yl |
| B.165 | 6-Methylpyrimidin-4-yl |
| B.166 | 6-Trifluoromethylpyrimidin-4-yl |
| B.167 | 6-Methoxypyrimidin-4-yl |
| B.168 | 2-Fluoropyrimidin-5-yl |
| B.169 | 2-Chloropyrimidin-5-yl |
| B.170 | 2-Bromopyrimidin-5-yl |
| B.171 | 2-Methylpyrimidin-5-yl |
| B.172 | 2-Trifluoromethylpyrimidin-5-yl |
| B.173 | 2-Methoxypyrimidin-5-yl |
| B.174 | 4-Fluoropyrimidin-5-yl |
| B.175 | 4-Chloropyrimidin-5-yl |
| B.176 | 4-Bromopyrimidin-5-yl |
| B.177 | 4-Methylpyrimidin-5-yl |
| B.178 | 4-Trifluoromethylpyrimidin-5-yl |
| B.179 | 3-Fluoro-5-trifluoromethylpyridin-2-yl |
| B.180 | 3,6-Dichloro-5-trifluoromethylpyridin-2-yl |
| B.181 | 5,6-Dichloro-3-trifluoromethylpyridin-2-yl |
| B.182 | 5-Chloro-3-trifluoromethylpyridin-2-yl |
| B.183 | 3-Chloro-5-trifluoromethylpyridin-2-yl |
| B.184 | 6-Chloro-4-cyanopyridin-2-yl |
| B.185 | 3-Cyano-5-nitropyridin-2-yl |
| B.186 | 2-Chloro-6-fluoropyridin-4-yl |
| B.187 | 6-Chloro-4-fluoropyridin-2-yl |
| B.188 | 4,6-Difluoropyridin-2-yl |
| B.189 | 3,5-Dichloro-6-fluoropyridin-2-yl |
| B.190 | 6-Methoxy-3-nitropyridin-2-yl |
| B.191 | 4-Cyano-6-fluoropyridin-2-yl |
| B.192 | 6-Chloro-5-cyanopyridin-2-yl |
| B.193 | 6-Chloro-3-cyanopyridin-2-yl |
| B.194 | 4-Cyano-3,5,6-trifluoropyridin-2-yl |
| B.195 | 6-Chloro-5-nitropyridin-2-yl |
| B.196 | 6-Chloro-3-nitropyridin-2-yl |
| B.197 | 5-Cyano-6-fluoropyridin-2-yl |
| B.198 | 3-Cyano-6-fluoropyridin-2-yl |
| B.199 | 4,6-Dicyanopyridin-2-yl |
| B.200 | 5-Trichloromethylpyridin-2-yl |
| B.201 | 5-Cyanopyridin-2-yl |
| B.202 | 5-Bromo-4-trifluoromethylpyridin-2-yl |
| B.203 | 3-Nitro-5-trifluoromethylpyridin-2-yl |
| B.204 | 5-Formamidopyridin-2-yl |
| B.205 | 5-Aminopyridin-2-yl |
| B.206 | 2,3,5,6-Tetrafluoropyridin-4-yl |
| B.207 | 5-Nitropyridin-2-yl |
| B.208 | 4-Methyl-5-nitropyridin-2-yl |
| B.209 | 5-Difluoromethylpyridin-2-yl |
| B.210 | 5-Fluoromethylpyridin-2-yl |
| B.211 | 4,6-Difluoropyrimidin-2-yl |
| B.212 | 2,6-Difluoropyrimidin-4-yl |
| B.213 | 2-Chloro-6-trichloromethylpyrimidin-4-yl |
| B.214 | 2,6-Dichloropyrimidin-4-yl |
| B.215 | 5-Methoxycarbonylpyridin-2-yl |
| B.216 | 5-Chloro-6-fluoropyridin-2-yl |
| B.217 | 5-Chloro-6-hydroxypyridin-2-yl |
| B.218 | 5-Chloro-6-methoxypyridin-2-yl |
| B.219 | 5-Chloro-6-cyanopyridin-2-yl |
| B.220 | 5,6-Dichloropyridin-2-yl |
| B.221 | 6-Bromo-5-chloropyridin-2-yl |
| B.222 | 5-Chloro-6-acetoxypyridin-2-yl |
| B.223 | 5-Bromo-6-fluoropyridin-2-yl |
| B.224 | 5-Bromo-6-chloropyridin-2-yl |
| B.225 | 5-Bromo-6-cyanopyridin-2-yl |
| B.226 | 5-Bromo-6-hydroxypyridin-2-yl |
| B.227 | 5-Bromo-6-methoxypyridin-2-yl |
| B.228 | 5,6-Dibromopyridin-2-yl |
| B.229 | 4-Cyanopyridin-2-yl |
| B.230 | 6-Cyanopyridin-2-yl |
| B.231 | 5-Chloropyridin-2-yl |
| B.232 | 5-Chloropyridin-2-yl |
| B.233 | 4-Chloro-6-methylpyrimidin-2-yl |
| B.234 | 2-Chloro-6-fluoropyridin-4-yl |
| B.235 | 5-Bromo-4-trifluoromethylpyridin-2-yl |
| B.236 | 4,5-Dichloropyridin-2-yl |
| B.237 | 4,5-Dibromopyridin-2-yl |
| B.238 | 5,6-Dichloropyridin-2-yl |
| B.239 | 4,6-Dichloropyridin-2-yl |
| B.240 | 4,6-Dibromopyridin-2-yl |
| B.241 | 5,6-Dibromopyridin-2-yl |
| B.242 | 4-Bromo-5-chloropyridin-2-yl |
| B.243 | 6-Bromo-5-chloropyridin-2-yl |
| B.244 | 5-Bromo-4-chloropyridin-2-yl |
| B.245 | 5-Bromo-4-chloropyridin-2-1yl |
| B.246 | 6-Bromo-4-chloropyridin-2-yl |
| B.247 | 4-Bromo-6-chloropyridin-2-yl |
| B.248 | 6-Chloro-4-methoxypyridin-2-yl |
| B.249 | 6-Bromo-4-methoxypyridin-2-yl |
| B.250 | 6-Chloroquinazolin-2-yl |
| B.251 | Quinazolin-2-yl |
| B.252 | 5-Benzyloxycarbonylpyridin-2-yl |
| B.253 | 4-Formylpyridin-2-yl |
| B.254 | 5-Formylpyridin-2-yl |
| B.255 | 6-Formylpyridin-2-yl |
| B.256 | 4-Cyanopyridin-2-yl |
| B.257 | 6-Cyanopyridin-2-yl |
| B.258 | 5-Hydroxymethylpyridin-2-yl |
| B.259 | 6-Chloro-4-trifluoromethylpyridin-2-yl |
| B.260 | 6-Chloro-4-trifluoromethylpyridin-2-yl |
| B.261 | 6-Chloro-4-methylpyridin-2-yl |
| B.262 | 2,5-Dichloro-6-cyanopyridin-2-yl |
| B.263 | 2,5-Dichloro-6-carboxypyridin-2-yl |
| B.264 | 2,5-Dichloro-6-methoxycarbonyl-pyridin-2-yl |
| B.265 | 4-Cyanopyridin-2-yl |
| B.266 | 6-Trifluoromethylpyridin-2-yl |
| B.267 | 6-Methoxycarbonylpyridin-2-yl |
| B.268 | 6-Carboxypyridin-2-yl |
| B.269 | 4-Phenoxypyridin-2-yl |
| B.270 | 5-Phenoxypyridin-2-yl |
| B.271 | 6-Phenoxypyridin-2-yl |
| B.272 | 6-Chloropyridin-3-yl |
| B.273 | 1-Phenoxypyrimidin-4-yl |
| B.274 | 1-(4-Methylphenoxy)pyrimidin-4-yl |
| B.275 | 4-Phenoxypyrimidin-2-yl |
| B.276 | 4-(2-Fluorophenoxy)pyrimidin-2-yl |
| B.277 | 4-Phenoxypyrimidin-6-yl |
| B.278 | 4-(4-Chlorophenoxy)pyrimidin-6-yl |
| B.279 | 4-(2-Pyridyloxy)pyrimidin-6-yl |
| B.280 | 4-(6-Chloro-2-pyridyloxy)pyrimidin-6-yl |
| B.281 | 4-(3-Pyridyloxy)pyrimidin-6-yl |
| B.282 | 4-(2-Methyl-3-pyridyloxy)pyrimidin-6-yl |
| B.283 | 4-(4-Pyridyloxy)pyrimidin-6-yl |
| B.284 | 2-Furanyl |

TABLE B-continued

| | |
|---|---|
| B.285 | 3-Furanyl |
| B.286 | 4-Chloro-2-thienyl |
| B.287 | 5-Chloro-2-thienyl |
| B.288 | 5-Bromo-2-thienyl |
| B.289 | 5-Nitro-2-thienyl |
| B.290 | 3-Thienyl |
| B.291 | 2-Chloro-3-thienyl |
| B.292 | 2-Bromo-3-thienyl |
| B.293 | 1-Methyl-3-pyrrolyl |
| B.294 | 1-Methyl-2-pyrroiyl |
| B.295 | 1-Benzofuran-2-yl |
| B.296 | 1-Benzofuran-3-yl |
| B.297 | 1-Benzothiophen-2-yl |
| B.298 | 1-Benzothiophen-3-yl |
| B.299 | 3-Pyrrolyl |
| B.300 | 2-Pyrrolyl |
| B.301 | 3-Indolyl |
| B.302 | 2-Indolyl |
| B.303 | 1-Methyl-3-indolyl |
| B.304 | 1-Methyl-2-indolyl |
| B.305 | 1-Methylpyrazol-4-yl |
| B.306 | 1-Methylpyrazol-3-yl |
| B.307 | 1-Methylpyrazol-5-yl |
| B.308 | Isoxazol-3-yl |
| B.309 | Isoxazol-4-yl |
| B.310 | Isoxazol-5-yl |
| B.311 | Isothiazol-3-yl |
| B.312 | Isothiazol-4-yl |
| B.313 | Isothiazol-5-yl |
| B.314 | Oxazol-2-yl |
| B.315 | Oxazol-5-yl |
| B.316 | Oxazol-4-yl |
| B.317 | Thiazol-4-yl |
| B.318 | Thiazol-5-yl |
| B.319 | Thiazol-2-yl |
| B.320 | 1-Methylimidazol-4-yl |
| B.321 | 1-Methylimidazol-5-yl |
| B.322 | 1-Methylimidazol-2-yl |
| B.323 | 1,2-Benzisoxazol-3-yl |
| B.324 | 1,2-Benzisothiazol-3-yl |
| B.325 | 1-Methylindazol-3-yl |
| B.326 | Benzoxazol-2-yl |
| B.327 | 5-Chlorobenzoxazol-2-yl |
| B.328 | 6-Fluorobenzoxazol-2-yl |
| B.329 | Benzthiazol-2-yl |
| B.330 | 5-Fluorobenzothiazol-2-yl |
| B.331 | 6-Fluorobenzothiazol-2-yl |
| B.332 | Pyrido[3,2-d]thiazol-2-yl |
| B.333 | (6-Chloropyrido)[3,2-d]thiazol-2-yl |
| B.334 | 1-Methyl-1,2,3-triazol-5-yl |
| B.335 | 1-Methyl-1,2,3-triazol-4-yl |
| B.336 | 1-Methyl-1,3,4-triazol-5-yl |
| B.337 | 1-Methyl-1,3,4-triazol-3-yl |
| B.338 | 1-Methyl-1,2,3,4-tetrazol-5-yl |
| B.339 | 2-Methyl-1,2,3,4-tetrazol-5-yl |
| B.340 | 5-Trifluoromethyl-1,3,4-thiadiazol-2-yl |
| B.341 | 6-Chlorobenzoxazol-2-yl |
| B.342 | 5-Fluorobenzoxazol-2-yl |
| B.343 | 5-Nitrothiazol-2-yl |

TABLE C

| | |
|---|---|
| C.1 | Phenyl |
| C.2 | 2-Fluorophenyl |
| C.3 | 3-Fluorophenyl |
| C.4 | 4-Fluorophenyl |
| C.5 | Pentafluorophenyl |
| C.6 | Pentafluorophenyl |
| C.7 | Pentafluorophenyl |
| C.8 | Pentafluorophenyl |
| C.9 | Pentafluorophenyl |
| C.10 | Pentafluorophenyl |
| C.11 | Pentafluorophenyl |
| C.12 | Pentafluorophenyl |
| C.13 | 2-Chlorophenyl |
| C.14 | 3-Chlorophenyl |

TABLE C-continued

| | |
|---|---|
| C.15 | 4-Chlorophenyl |
| C.16 | Pentachlorophenyl |
| C.17 | 2,3-Dichlorophenyl |
| C.18 | 2,4-Dichlorophenyl |
| C.19 | 2,5-Dichlorophenyl |
| C.20 | 2,6-Dichlorophenyl |
| C.21 | 3,4-Dichlorophenyl |
| C.22 | 3,5-Dichlorophenyl |
| C.23 | 2,3,4-Trichlorophenyl |
| C.24 | 2,3,5-Trichlorophenyl |
| C.25 | 2,3,6-Trichlorophenyl |
| C.26 | 2-Cyanophenyl |
| C.27 | 3-Cyanophenyl |
| C.28 | 4-Cyanophenyl |
| C.29 | 2-Nitrophenyl |
| C.30 | 3-Nitrophenyl |
| C.31 | 4-Nitrophenyl |
| C.32 | 2-Methylphenyl |
| C.33 | 3-Methylphenyl |
| C.34 | 4-Methylphenyl |
| C.35 | 2,4-Dimethylphenyl |
| C.36 | 2,6-Dimethylphenyl |
| C.37 | 3,4-Dimethylphenyl |
| C.38 | 3,5-Dimethylphenyl |
| C.39 | 2,3,4-Trimethylphenyl |
| C.40 | 2,3,5-Trimethylphenyl |
| C.41 | 2,3,6-Trimethylphenyl |
| C.42 | 2,4,5-Trimethylphenyl |
| C.43 | 2,4,6-Trimethylphenyl |
| C.44 | 3,4,5-Trimethylphenyl |
| C.45 | Pentamethylphenyl |
| C.46 | 2-Ethylphenyl |
| C.47 | 3-Ethylphenyl |
| C.48 | 4-Ethylphenyl |
| C.49 | 3,5-Diethylphenyl |
| C.50 | 2-n-Propylphenyl |
| C.51 | 3-n-Propylphenyl |
| C.52 | 4-n-Propylphenyl |
| C.53 | 2-Isopropylphenyl |
| C.54 | 3-Isopropylphenyl |
| C.55 | 4-Isopropylphenyl |
| C.56 | 2,4-Di-iso-Propylphenyl |
| C.57 | 3,5-Di-iso-Propylphenyl |
| C.58 | 4-n-Butylphenyl |
| C.59 | 4-sec-Butylphenyl |
| C.60 | 4-iso-Butylphenyl |
| C.61 | 4-tert-Butylphenyl |
| C.62 | 3-tert-Butylphenyl |
| C.63 | 2-tert-Butylphenyl |
| C.64 | 2,4-Di-tert-Butylphenyl |
| C.65 | 2,5-Di-tert-Butylphenyl |
| C.66 | 4-n-Hexylphenyl |
| C.67 | 4-n-Dodecylphenyl |
| C.68 | 2-Methyl-4-tert-butylphenyl |
| C.69 | 2-Methyl-6-tert-butylphenyl |
| C.70 | 2-Methyl-4-iso-propylphenyl |
| C.71 | 2-Methyl-4-cyclohexylphenyl |
| C.72 | 2-Methyl-4-phenylphenyl |
| C.73 | 2-Methyl-4-benzylphenyl |
| C.74 | 2-Methyl-5-phenoxyphenyl |
| C.75 | 2-Methyl-4-benzyloxyphenyl |
| C.76 | 2-Methyl-3-chlorophenyl |
| C.77 | 2-Methyl-4-chlorophenyl |
| C.78 | 2-Methyl-5-chlorophenyl |
| C.79 | 2-Methyl-6-chlorophenyl |
| C.80 | 2-Methyl-4-fluorophenyl |
| C.81 | 2-Methyl-3-bromophenyl |
| C.82 | 2-Methyl-4-bromophenyl |
| C.83 | 2-Methyl-3-methoxyphenyl |
| C.84 | 2-Methyl-4-methoxyphenyl |
| C.85 | 2-Methyl-5-methoxyphenyl |
| C.86 | 2-Methyl-6-methoxyphenyl |
| C.87 | 2-Methyl-4-isopropoxyphenyl |
| C.88 | 2-Methyl-2,5-dimethoxyphenyl |
| C.89 | 2-Methoxyphenyl |
| C.90 | 3-Methoxyphenyl |
| C.91 | 4-Methoxyphenyl |
| C.92 | 2,3-Dimethoxyphenyl |
| C.93 | 2,4-Dimethoxyphenyl |

TABLE C-continued

| | |
|---|---|
| C.94 | 2,5-Dimethoxyphenyl |
| C.95 | 2,6-Dimethoxyphenyl |
| C.96 | 3,4-Dimethoxyphenyl |
| C.97 | 3,5-Dimethoxyphenyl |
| C.98 | 3,6-Dimethoxyphenyl |
| C.99 | 2,3,4-Trimethoxyphenyl |
| C.100 | 2,3,5-Trimethoxyphenyl |
| C.101 | 2,3,6-Trimethoxyphenyl |
| C.102 | 2,4,5-Trimethoxyphenyl |
| C.103 | 2,4,6-Trimethoxyphenyl |
| C.104 | 3,4,5-Trimethoxyphenyl |
| C.105 | 2-Ethoxyphenyl |
| C.106 | 3-Ethoxyphenyl |
| C.107 | 4-Ethoxyphenyl |
| C.108 | 2-Isopropoxyphenyl |
| C.109 | 3-Isopropoxyphenyl |
| C.110 | 4-Isopropoxyphenyl |
| C.111 | 3-tert-Butoxyphenyl |
| C.112 | 4-tert-Butoxyphenyl |
| C.113 | 2-Trifluoromethoxyphenyl |
| C.114 | 3-Trifluoromethoxyphenyl |
| C.115 | 4-Trifluoromethoxyphenyl |
| C.116 | 3-(1',1',2',2'-Tetrafluoro)ethoxyphenyl |
| C.117 | 4-(1',1',2',2'-Tetrafluoro)ethoxyphenyl |
| C.118 | 2-Chloromethylphenyl |
| C.119 | 3-Chloromethylphenyl |
| C.120 | 4-Chloromethylphenyl |
| C.121 | 2-Trifluoromethylphenyl |
| C.122 | 3-Trifluoromethylphenyl |
| C.123 | 4-Trifluoromethylphenyl |
| C.124 | 2-(Methoxyiminomethyl)phenyl |
| C.125 | 3-(Methoxyiminomethyl)phenyl |
| C.126 | 4-(Methoxyiminomethyl)phenyl |
| C.127 | 2-(Ethoxyiminomethyl)phenyl |
| C.128 | 3-(Ethoxyiminomethyl)phenyl |
| C.129 | 4-(Ethoxyiminomethyl)phenyl |
| C.130 | 2-(n-Propoxyiminomethyl)phenyl |
| C.131 | 3-(n-Propoxyiminomethyl)phenyl |
| C.132 | 4-(n-Propoxyiminomethyl)phenyl |
| C.133 | 2-(iso-Propoxyiminomethyl)phenyl |
| C.134 | 3-(iso-Propoxyiminomethyl)phenyl |
| C.135 | 4-(iso-Propoxyiminomethyl)phenyl |
| C.136 | 2-(n-Butoxyiminomethyl)phenyl |
| C.137 | 3-(n-Butoxyiminomethyl)phenyl |
| C.138 | 4-(n-Butoxyiminomethyl)phenyl |
| C.139 | 2-(iso-Butoxyiminomethyl)phenyl |
| C.140 | 3-(iso-Butoxyiminomethyl)phenyl |
| C.141 | 4-(iso-Butoxyiminomethyl)phenyl |
| C.142 | 2-(tert-Butoxyiminomethyl)phenyl |
| C.143 | 3-(tert-Butoxyiminomethyl)phenyl |
| C.144 | 4-(tert-Butoxyiminomethyl)phenyl |
| C.145 | 2-(n-Pentoxyiminomethyl)phenyl |
| C.146 | 3-(n-Pentoxyiminomethyl)phenyl |
| C.147 | 4-(n-Pentoxyiminomethyl)phenyl |
| C.148 | 2-(n-Hexoxyiminomethyl)phenyl |
| C.149 | 3-(n-Hexoxyiminomethyl)phenyl |
| C.150 | 4-(n-Hexoxyiminomethyl)phenyl |
| C.151 | 2-(Allyloxyimonomethyl)phenyl |
| C.152 | 3-(Allyloxyimonomethyl)phenyl |
| C.153 | 4-(Allyloxyimonomethyl)phenyl |
| C.154 | 2-(Benzyloxyiminomethyl)phenyl |
| C.155 | 3-(Benzyloxyiminomethyl)phenyl |
| C.156 | 4-(Benzyloxyiminomethyl)phenyl |
| C.157 | 2-(Methoxyimino-1'-ethyl)phenyl |
| C.158 | 3-(Methoxyimino-1'-ethyl)phenyl |
| C.159 | 4-(Methoxyimino-1'-ethyl)phenyl |
| C.160 | 2-(Ethoxyimino-1'-ethyl)phenyl |
| C.161 | 3-(Ethoxyimino-1'-ethyl)phenyl |
| C.162 | 4-(Ethoxyimino-1'-ethyl)phenyl |
| C.163 | 2-(n-Propoxyimino-1'-ethyl)phenyl |
| C.164 | 3-(n-Propoxyimino-1'-ethyl)phenyl |
| C.165 | 4-(n-Propoxyimino-1'-ethyl)phenyl |
| C.166 | 2-(n-Butoxyamino-1'-ethyl)phenyl |
| C.167 | 3-(n-Butoxyamino-1'-ethyl)phenyl |
| C.168 | 4-(n-Butoxyamino-1'-ethyl)phenyl |
| C.169 | 2-(n-Butoxyamino-1'-ethyl)phenyl |
| C.170 | 3-(n-Butoxyamino-1'-ethyl)phenyl |
| C.171 | 4-(n-Butoxyamino-1'-ethyl)phenyl |
| C.172 | 2-(n-Pentoxyimino-1'-ethyl)phenyl |
| C.173 | 3-(n-Pentoxyimino-1'-ethyl)phenyl |
| C.174 | 4-(n-Pentoxyimino-1'-ethyl)phenyl |
| C.175 | 2-(n-Pentoxyimino-1'-ethyl)phenyl |
| C.176 | 3-(n-Pentoxyimino-1'-ethyl)phenyl |
| C.177 | 4-(n-Pentoxyimino-1'-ethyl)phenyl |
| C.178 | 2-(n-Hexoxyimino-1'-ethyl)phenyl |
| C.179 | 3-(n-Hexoxyimino-1'-ethyl)phenyl |
| C.180 | 4-(n-Hexoxyimino-1'-ethyl)phenyl |
| C.181 | 2-(Allyloxyimino-1'-ethyl)phenyl |
| C.182 | 3-(Allyloxyimino-1'-ethyl)phenyl |
| C.183 | 4-(Allyloxyimino-1'-ethyl)phenyl |
| C.184 | 2-(Benzyloxyimino-1'-ethyl)phenyl |
| C.185 | 3-(Benzyloxyimino-1'-ethyl)phenyl |
| C.186 | 4-(Benzyloxyimino-1'-ethyl)phenyl |
| C.187 | 2-Phenylphenyl |
| C.188 | 3-Phenylphenyl |
| C.189 | 4-Phenylphenyl |
| C.190 | 2-Phenoxyphenyl |
| C.191 | 3-Phenoxyphenyl |
| C.192 | 4-Phenoxyphenyl |
| C.193 | 2-Benzyloxyphenyl |
| C.194 | 3-Benzyloxyphenyl |
| C.195 | 4-Benzyloxyphenyl |
| C.196 | 4-(Imidazol-1'-yl)phenyl |
| C.197 | 4-(Piperazin-1'-yl)phenyl |
| C.198 | 4-(Morpholin-1'-yl)phenyl |
| C.199 | 4-(Piperidin-1'-yl)phenyl |
| C.200 | 4-(Pyridyl-2'-oxy)phenyl |
| C.201 | 2-Cyclopropylphenyl |
| C.202 | 3-Cyclopropylphenyl |
| C.203 | 4-Cyclopropylphenyl |
| C.204 | 3-Cyclohexylphenyl |
| C.205 | 4-Cyclohexylphenyl |
| C.206 | 4-Oxiranylphenyl |
| C.207 | 4-(1',3'-Dioxan-2'-yl)phenyl |
| C.208 | 4-(Tetrahydropyran-2-yloxy)phenyl |
| C.209 | 1-Naphthyl |
| C.210 | 2-Naphthyl |
| C.211 | 9-Anthryl |
| C.212 | 1-Naphthoxy |
| C.213 | 2-Naphthoxy |
| C.214 | 9-Anthroxy |
| C.215 | Phenoxy |
| C.216 | 2-Chlorophenoxy |
| C.217 | 3-Chlorophenoxy |
| C.218 | 4-Chlorophenoxy |
| C.219 | 4-tert-Butylphenoxy |
| C.220 | 4-Methoxyphenoxy |
| C.221 | 4-Ethoxyphenoxy |
| C.222 | 4-tert-Butoxyphenoxy |
| C.223 | Phenylthio |
| C.224 | 2-Chlorophenylthio |
| C.225 | 4-Chlorophenylthio |
| C.226 | Benzyl |
| C.227 | 2-Methylbenzyl |
| C.228 | 3-Methylbenzyl |
| C.229 | 4-Methylbenzyl |
| C.230 | 4-tert-Butylbenzyl |
| C.231 | 2-Chlorobenzyl |
| C.232 | 3-Chlorobenzyl |
| C.233 | 4-Chlorobenzyl |
| C.234 | 2,4-Dichlorobenzyl |
| C.235 | 2,6-Dichlorobenzyl |
| C.236 | 2,4,6-Trichlorobenzyl |
| C.237 | 2-Trifluoromethylbenzyl |
| C.238 | 3-Trifluoromethylbenzyl |
| C.239 | 4-Trifluoromethylbenzyl |
| C.240 | 2-Methoxybenzyl |
| C.241 | 4-Methoxybenzyl |
| C.242 | 4-tert-Butoxybenzyl |
| C.243 | 4-Phenoxybenzyl |
| C.244 | 1-Phenethyl |
| C.245 | 2-Phenethyl |
| C.246 | 1-Phenylpropyl |
| C.247 | 2-Phenylpropyl |
| C.248 | 3-Phenylpropyl |
| C.249 | 2-Methyl-2-phenylpropyl |
| C.250 | 2-Methyl-3-phenylpropyl |
| C.251 | 4-Phenylbutyl |

TABLE C-continued

| No. | |
|---|---|
| C.252 | 2-Phenyl-1-ethenyl |
| C.253 | 1-Phenyl-1-ethenyl |
| C.254 | 1-Phenyl-1-propenyl |
| C.255 | 1-Phenyl-1-propen-2-yl |
| C.256 | 2,2-Diphenylethenyl |
| C.257 | Phenoxymethyl |
| C.258 | 3-Pyridyl |
| C.259 | 3-Pyridyl |
| C.260 | 4-Pyridyl |
| C.261 | 2,6-Pyrimidinyl |
| C.262 | 1,5-Pyrimidinyl |
| C.263 | 2-Thienyl |
| C.264 | 3-Thienyl |
| C.265 | 2-Furyl |
| C.266 | 3-Furyl |
| C.267 | 1-Pyrrolyl |
| C.268 | 1-Imidazolyl |
| C.269 | 1,3,4-Triazolyl |
| C.270 | 1,3,4-Triazolyl |
| C.271 | 4-Thiazolyl |
| C.272 | 2-Benzothiazolyl |
| C.273 | 2-Pyridyloxy |
| C.274 | 2-Pyrimidinyloxy |
| C.275 | 2-Pyridylthio |
| C.276 | 2-Pyrimidinylthio |
| C.277 | 2-Benzothiazolylthio |
| C.278 | Phenylthiomethyl |
| C.279 | 2-Pyridylmethyl |
| C.280 | 3-Pyridylmethyl |
| C.281 | Furfuryloxy |
| C.282 | Thienylmethoxy |
| C.283 | 2-Isoxazolylmethoxy |
| C.284 | 2-Oxazolylmethoxy |
| C.285 | 2-Pyridylmethoxy |
| C.286 | 2'-Furylethenyl |
| C.287 | 2'-Thienyl-2-ethenyl |
| C.288 | 3'-Pyridyl-2-ethenyl |
| C.289 | Oxiranyl |
| C.290 | 1-Aziridinyl |
| C.291 | 1-Azetidinyl |
| C.292 | 1-Pyrrolidinyl |
| C.293 | 2-Tetrahydrofuryl |
| C.294 | 2-Tetrahydropyranyl |
| C.295 | 3-Tetrahydropyranyl |
| C.296 | 1-Piperidinyl |
| C.297 | 1-Morpholinyl |
| C.298 | 1-Piperazinyl |
| C.299 | 1,3-Dioxan-2-yl |
| C.300 | 3-Tetrahydrothiopyranyl |
| C.301 | 2-Dihydropyranyloxy |
| C.302 | 2-Tetrahydropyranyloxy |
| C.303 | Cyclopropyl |
| C.304 | Cyclobutyl |
| C.305 | Cyclopentyl |
| C.306 | Cyclohexyl |
| C.307 | 1-Methylcyclopropyl |
| C.308 | 2,2-Dimethylcyclopropyl |
| C.309 | 1-Methylcyclohexyl |
| C.310 | 2,2-Difluorocyclopropyl |
| C.311 | 2,2-Dichlorocyclopropyl |
| C.312 | 2,2-Dibromocyclopropyl |
| C.313 | 2,2,-Dichloro-3-Methylcyclopropyl |
| C.314 | 2,2,3,3,-Tetrafluorocyclobutyl |
| C.315 | $CH_3$ |
| C.316 | $CH_3CH_2$ |
| C.317 | $CH_3CH_2CH_2$ |
| C.318 | $CH_2=CH-CH_2$ |
| C.319 | $HC\equiv C-CH_2$ |
| C.320 | $(CH_3)_3C$ |
| C.321 | Cyclo-$C_6H_{11}$ |
| C.322 | $C_6H_5-CH_2-$ |
| C.323 | $C_6H_5-CH_2O-$ |
| C.324 | $(CH_3)_2CH$ |
| C.325 | $CH_3O-CH_2$ |

TABLE D

| No. | Y | $R^4$ |
|---|---|---|
| D.1 | $CH_3$ | H |
| D.2 | $CH_3$ | $CH_3$ |
| D.3 | $CH_3$ | $C_2H_5$ |
| D.4 | $CH_3$ | n-$C_3H_7$ |
| D.5 | $CH_3$ | i-$C_3H_7$ |
| D.6 | $CH_3$ | Cyclopropyl |
| D.7 | $CH_3$ | n-$C_4H_9$ |
| D.8 | $CH_3$ | s-$C_4H_9$ |
| D.9 | $CH_3$ | i-$C_4H_9$ |
| D.10 | $CH_3$ | t-$C_4H_9$ |
| D.11 | $CH_3$ | n-$C_5H_{11}$ |
| D.12 | $CH_3$ | i-$C_5H_{11}$ |
| D.13 | $CH_3$ | neo-$C_5H_{11}$ |
| D.14 | $CH_3$ | Cyclopentyl |
| D.15 | $CH_3$ | n-$C_6H_{13}$ |
| D.16 | $CH_3$ | Cyclohexyl |
| D.17 | $CH_3$ | n-$C_8H_{17}$ |
| D.18 | $CH_3$ | $CH_2CH_2Cl$ |
| D.19 | $CH_3$ | $(CH_2)_4Cl$ |
| D.20 | $CH_3$ | $CH_2CN$ |
| D.21 | $CH_3$ | $CH_2CH_2CN$ |
| D.22 | $CH_3$ | $(CH_2)_3CN$ |
| D.23 | $CH_3$ | $(CH_2)_4CN$ |
| D.24 | $CH_3$ | $(CH_2)_6CN$ |
| D.25 | $CH_3$ | Cyclopropylmethyl |
| D.26 | $CH_3$ | 2-Methoxyeth-1-yl |
| D.27 | $CH_3$ | 2-Ethoxyeth-1-yl |
| D.28 | $CH_3$ | 2-Isopropoxyeth-1-yl |
| D.29 | $CH_3$ | 3-Methoxyprop-1-yl |
| D.30 | $CH_3$ | 3-Ethoxyprop-1-yl |
| D.31 | $CH_3$ | 3-Isopropoxyprop-1-yl |
| D.32 | $CH_3$ | 4-Methoxybut-1-yl |
| D.33 | $CH_3$ | 4-Isopropoxybut-1-yl |
| D.34 | $CH_3$ | Propen-3-yl |
| D.35 | $CH_3$ | But-2-en-1-yl |
| D.36 | $CH_3$ | 3-Methylbut-2-en-1-yl |
| D.37 | $CH_3$ | 2-Vinyloxyeth-1-yl |
| D.38 | $CH_3$ | Allyloxyeth-1-yl |
| D.39 | $CH_3$ | 2-Trifluoromethoxyeth-1-yl |
| D.40 | $CH_3$ | 3-Trifluoromethoxyprop-1-yl |
| D.41 | $CH_3$ | 4-Difluoromethoxybut-1-yl |
| D.42 | $CH_3$ | 2-Oxopropyl |
| D.43 | $CH_3$ | Cyclohexyl |
| D.44 | $CH_3$ | Cyclopropyl |
| D.45 | $CH_3$ | Cyclopentyl |
| D.46 | 4-F—$C_6H_4$ | H |
| D.47 | 4-F—$C_6H_4$ | $CH_3$ |
| D.48 | 4-F—$C_6H_4$ | $C_2H_5$ |
| D.49 | 4-F—$C_6H_4$ | n-$C_3H_7$ |
| D.50 | 4-F—$C_6H_4$ | i-$C_3H_7$ |
| D.51 | 4-F—$C_6H_4$ | Cyclopropyl |
| D.52 | 4-F—$C_6H_4$ | n-$C_4H_9$ |
| D.53 | 4-F—$C_6H_4$ | t-$C_4H_9$ |
| D.54 | 4-F—$C_6H_4$ | n-$C_6H_{13}$ |
| D.55 | 4-F—$C_6H_4$ | (E)-1-Chloropropen-3-yl |
| D.56 | $CH_2CH_3$ | H |
| D.57 | $CH_2CH_3$ | $CH_3$ |
| D.58 | $CH_2CH_3$ | $CH_2CH_3$ |
| D.59 | $CH_2CH_3$ | n-$C_3H_7$ |
| D.60 | $CH_2CH_3$ | $CH_2-C\equiv CH$ |
| D.61 | $CH_2CH_3$ | $CH_2-CH=CH_2$ |
| D.62 | $CH_2CH_3$ | tert-$C_4H_9$ |
| D.63 | $C_6H_5$ | H |
| D.64 | $C_6H_5$ | $CH_3$ |
| D.65 | $C_6H_5$ | $C_2H_5$ |
| D.66 | $C_6H_5$ | n-$C_3H_7$ |
| D.67 | $C_6H_5$ | i-$C_3H_7$ |
| D.68 | $C_6H_5$ | Cyclopropyl |
| D.69 | $C_6H_5$ | n-$C_4H_9$ |
| D.70 | $C_6H_5$ | t-$C_4H_9$ |
| D.71 | $C_6H_5$ | n-$C_6H_{13}$ |
| D.72 | O—i-$C_3H_7$ | $CH_3$ |
| D.73 | O—i-$C_3H_7$ | $CH_2CH_3$ |
| D.74 | O—$CH_2CH_3$ | $CH_3$ |
| D.75 | O—$CH_2CH_3$ | $CH_2CH_3$ |
| D.76 | O—Cyclopropyl | $CH_3$ |
| D.77 | H | $CH_3$ |

TABLE D-continued

| No. | Y | R⁴ |
|---|---|---|
| D.78 | H | C₂H₅ |
| D.79 | O—CH(CH₂CH₃)₂ | CH₃ |
| D.80 | O—CH(CH₂CH₃)₂ | CH₂CH₃ |
| D.81 | O—Cyclopentyl | CH₃ |
| D.82 | OH | CH₃ |
| D.83 | OH | C₂H₅ |
| D.84 | OH | n-C₃H₇ |
| D.85 | OH | i-C₃H₇ |
| D.86 | Cl | CH₃ |
| D.87 | Cl | C₂H₅ |
| D.88 | Cl | n-C₃H₇ |
| D.89 | Cl | i-C₃H₇ |
| D.90 | OCH₃ | H |
| D.91 | OCH₃ | CH₃ |
| D.92 | OCH₃ | C₂H₅ |
| D.93 | OCH₃ | n-C₃H₇ |
| D.94 | OCH₃ | i-C₃H₇ |
| D.95 | SCH₃ | H |
| D.96 | SCH₃ | CH₃ |
| D.97 | SCH₃ | C₂H₅ |
| D.98 | O—Cyclohexyl | CH₃ |
| D.99 | O—Cyclohexyl | CH₂CH₃ |
| D.100 | Cyclopropyl | H |
| D.101 | Cyclopropyl | CH₃ |
| D.102 | Cyclopropyl | C₂H₅ |
| D.103 | Cyclopropyl | n-C₃H₇ |
| D.104 | Cyclopropyl | i-C₃H₇ |
| D.105 | 2-Pyridyl | H |
| D.106 | 2-Pyridyl | CH₃ |
| D.107 | 2-Pyridyl | C₂H₅ |
| D.108 | 2-Pyridyl | n-C₃H₇ |
| D.109 | 2-Pyridyl | i-C₃H₇ |
| D.110 | 3-Pyridyl | H |
| D.111 | 3-Pyridyl | CH₃ |
| D.112 | 3-Pyridyl | C₂H₅ |
| D.113 | 3-Pyridyl | n-C₃H₇ |
| D.114 | 3-Pyridyl | i-C₃H₇ |
| D.115 | 4-Pyridyl | H |
| D.116 | 4-Pyridyl | CH₃ |
| D.117 | 4-Pyridyl | C₂H₅ |
| D.118 | 4-Pyridyl | n-C₃H₇ |
| D.119 | 4-Pyridyl | i-C₃H₇ |
| D.120 | 2-Pyridimidyl | H |
| D.121 | 2-Pyridimidyl | CH₃ |
| D.122 | 2-Pyridimidyl | C₂H₅ |
| D.123 | 2-Pyridimidyl | n-C₃H₇ |
| D.124 | 2-Pyridimidyl | i-C₃H₇ |
| D.125 | 4-Pyridimidyl | H |
| D.126 | 4-Pyridimidyl | CH₃ |
| D.127 | 4-Pyridimidyl | C₂H₅ |
| D.128 | 4-Pyridimidyl | n-C₃H₇ |
| D.129 | 4-Pyridimidyl | i-C₃H₇ |
| D.130 | 5-Pyridimidyl | H |
| D.131 | 5-Pyridimidyl | CH₃ |
| D.132 | 5-Pyridimidyl | C₂H₅ |
| D.133 | 5-Pyridimidyl | n-C₃H₇ |
| D.134 | 5-Pyridimidyl | i-C₃H₇ |
| D.135 | O—tert-Butyl | CH₃ |
| D.136 | O—tert-Butyl | CH₂CH₃ |
| D.137 | O—n-Propyl | CH₃ |
| D.138 | O—n-Butyl | CH₃ |
| D.139 | O—CH₂C₆H₅ | CH₃ |
| D.140 | 2-Furyl | H |
| D.141 | 2-Furyl | CH₃ |
| D.142 | O—n-Pentyl | CH₃ |
| D.143 | O—n-Hexyl | CH₃ |
| D.144 | 3-Furyl | H |
| D.145 | 3-Furyl | CH₃ |
| D.146 | 2-Oxazolyl | H |
| D.147 | 2-Oxazolyl | CH₃ |
| D.148 | 2-Oxazolyl | C₂H₅ |
| D.149 | 2-Oxazolyl | n-C₃H₇ |
| D.150 | 2-Oxazolyl | i-C₃H₇ |
| D.151 | 4-Oxazolyl | H |
| D.152 | 4-Oxazolyl | CH₃ |
| D.153 | 4-Oxazolyl | C₂H₅ |
| D.154 | 4-Oxazolyl | n-C₃H₇ |
| D.155 | 4-Oxazolyl | i-C₃H₇ |
| D.156 | 3-Isoxazolyl | H |
| D.157 | 3-Isoxazolyl | CH₃ |
| D.158 | 3-Isoxazolyl | C₂H₅ |
| D.159 | 3-Isoxazolyl | n-C₃H₇ |
| D.160 | 3-Isoxazolyl | i-C₃H₇ |
| D.161 | 5-Isoxazolyl | H |
| D.162 | 5-Isoxazolyl | CH₃ |
| D.163 | 5-Isoxazolyl | C₂H₅ |
| D.164 | 5-Isoxazolyl | n-C₃H₇ |
| D.165 | 5-Isoxazolyl | i-C₃H₇ |
| D.166 | 3-Pyrazolyl | H |
| D.167 | 3-Pyrazolyl | CH₃ |
| D.168 | 3-Pyrazolyl | C₂H₅ |
| D.169 | 3-Pyrazolyl | n-C₃H₇ |
| D.170 | 3-Pyrazolyl | i-C₃H₇ |
| D.171 | 4-Pyrazolyl | H |
| D.172 | 4-Pyrazolyl | CH₃ |
| D.173 | 4-Pyrazolyl | C₂H₅ |
| D.174 | 4-Pyrazolyl | n-C₃H₇ |
| D.175 | 4-Pyrazolyl | i-C₃H₇ |

TABLE E

| | |
|---|---|
| E.1 | C₆H₅ |
| E.2 | 2-F—C₆H₄ |
| E.3 | 3-F—C₆H₄ |
| E.4 | 4-F—C₆H₄ |
| E.5 | 2-Cl—C₆H₄ |
| E.6 | 3-Cl—C₆H₄ |
| E.7 | 4-Cl—C₆H₄ |
| E.8 | 2-CH₃—C₆H₄ |
| E.9 | 3-CH₃—C₆H₄ |
| E.10 | 4-CH₃—C₆H₄ |
| E.11 | 2,4-(CH₃)₂—C₆H₃ |
| E.12 | 2,6-(CH₃)₂—C₆H₃ |
| E.13 | 2,6-F₂—C₆H₃ |
| E.14 | 2,6-Cl₂—C₆H₃ |
| E.15 | 2,4-F₂—C₆H₃ |
| E.16 | 2,4-Cl₂—C₆H₃ |
| E.17 | 2,5-F₂—C₆H₃ |
| E.18 | 2,5-Cl₂—C₆H₃ |
| E.19 | 2,5-(CH₃)₂—C₆H₃ |
| E.20 | 2-OCH₃—C₆H₄ |
| E.21 | 3-OCH₃—C₆H₄ |
| E.22 | 4-OCH₃—C₆H₄ |
| E.23 | 2-CN—C₆H₄ |
| E.24 | 3-CN—C₆H₄ |
| E.25 | 4-CN—C₆H₄ |
| E.26 | 2-NO₂—C₆H₄ |
| E.27 | 3-NO₂—C₆H₄ |
| E.28 | 4-NO₂—C₆H₄ |
| E.29 | 2-CO₂CH₃—C₆H₄ |
| E.30 | 2-COCH₃—C₆H₄ |
| E.31 | 3-COCH₃—C₆H₄ |
| E.32 | 4-CO₂CH₃—C₆H₄ |
| E.33 | 4-COCH₃—C₆H₄ |
| E.34 | 2-CH₃-4-COCH₃—C₆H₃ |
| E.35 | CH₃ |
| E.36 | CH₂CH₃ |
| E.37 | CH₂CH₂CH₃ |
| E.38 | iso-Propyl |
| E.39 | n-Propyl |
| E.40 | tert-Butyl |
| E.41 | Hexyl |
| E.42 | Pentyl |
| E.43 | Isopropyl |
| E.44 | CH(CH₂CH₃)₂ |
| E.45 | CH₂CF₃ |
| E.46 | CF₃ |
| E.47 | CHF₂ |
| E.48 | CClF₂ |
| E.49 | 2-OH—C₆H₄ |
| E.50 | 2-NH—CONH₂—C₆H₄ |

TABLE E-continued

| | |
|---|---|
| E.51 | 2-NH—SO$_2$CH$_3$—C$_6$H$_4$ |
| E.52 | 2-SCN—C$_6$H$_4$ |
| E.53 | 3-SCN—C$_6$H$_4$ |
| E.54 | 4-SCN—C$_6$H$_4$ |
| E.55 | 2-SCH$_3$—C$_6$H$_4$ |
| E.56 | 3-SCH$_3$—C$_6$H$_4$ |
| E.57 | 4-SCH$_3$—C$_6$H$_4$ |
| E.58 | 2-CHO—C$_6$H$_4$ |
| E.59 | 3-CHO—C$_6$H$_4$ |
| E.60 | 4-CHO—C$_6$H$_4$ |
| E.61 | 2-CONH$_2$—C$_6$H$_4$ |
| E.62 | 3-CONH$_2$—C$_6$H$_4$ |
| E.63 | 4-CONH$_2$—C$_6$H$_4$ |
| E.64 | 2-CONH(CH$_3$)—C$_6$H$_4$ |
| E.65 | 2-CONH(CH$_3$)—C$_6$H$_4$ |
| E.66 | 4-CONH(CH$_3$)—C$_6$H$_4$ |
| E.67 | 3-iso-Propyl—C$_6$H$_4$ |
| E.68 | 4-iso-Propyl—C$_6$H$_4$ |
| E.69 | 3-tert-Butyl—C$_6$H$_4$ |
| E.70 | 4-tert-Butyl—C$_6$H$_4$ |

TABLE F

| No. | R$^1$ | R$^2$ | X | Y—A | Data mp. (° C.); IR (cm$^{-1}$); NMR (ppm) |
|---|---|---|---|---|---|
| F.1 | CH$_3$ | CH$_3$ | —C(CO$_2$CH$_3$)=NOCH$_3$ | CH$_3$ON=C(4-F—C$_6$H$_4$)—C(CH$_3$)=N—O— | 2.32 (s, 3H, CH$_3$), 2.54 (s, 3H, CH$_3$), 2.60 (s, 3H, CH$_3$), 3.76 (s, 3H, OCH$_3$), 4.0 (s, 3H, OCH$_3$), 4.06 (s, 3H, OCH$_3$), 7.1 (m, 2H, arom.), 7.46 (m, 2H, arom.). |

The compounds I are useful as fungicides.

The compounds I are distinguished by an outstanding activity against a broad spectrum of phytopathogenic fungi, in particular from the classes of the Ascomycetes and Basidiomycetes. Some of them act systemically and can be employed as foliar and soil fungicides.

They are especially important for controlling a large number of fungi in a variety of crop plants such as wheat, rye, barley, oats, rice, corn, grass, cotton, soybeans, coffee, sugar cane, grapevines, fruit species, ornamentals and vegetable species such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and Verticillium species on various plants, *Plasmopara viticola* on grapevines, Alternaria species on vegetables and fruit.

The compounds I are used by treating the fungi, or the plants, seeds, materials or the soil to be protected against fungal attack, with a fungicidally effective amount of the active ingredients. Application is effected before or after infection of the materials, plants or seeds by the fungi.

They can be converted into the customary formulations, such as solutions, emulsions, suspensions, dusts, powders, pastes and granules. The use form depends on the respective intended purpose; in any case, it should guarantee fine and uniform distribution of the compounds according to the invention. The formulations are prepared in a known manner, for example by extending the active ingredient with solvents and/or carriers, if desired using emulsifiers and dispersants, it also being possible to use other organic solvents as auxiliary solvents if water is used as the diluent. Suitable auxiliaries are essentially:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants, such as lignosulfite waste liquors and methylcellulose.

In general, the fungicidal compositions comprise from 0.1 to 95, preferably from 0.5 to 90, % by weight of active ingredient.

Depending on the nature of the desired effect, the rates of application are from 0.01 to 2.0 kg of active ingredient per ha.

For seed treatment, amounts of active ingredient of from 0.001 to 0.1 g, preferably 0.01 to 0.05 g, are generally required per kilogram of seed.

In the use form as fungicides, the compositions according to the invention can also be present together with other active ingredients, eg. with herbicides, insecticides, growth regulators, fungicides or alternatively fertilizers.

A mixture with fungicides frequently results in a widening of the fungicidal spectrum of action.

The following list of fungicides with which the compounds according to the invention can be used are intended to illustrate the possible combinations, but not to restrict them:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives such as dinitro(1-methylheptyl)phenyl crotonate, 2-sec-butyl-4,6-dinitrophenyl-3,3-dimethyl acrylate, 2-sec-butyl-4,6-dinitrophenyl isopropyl carbonate, diisopropyl 5-nitroisophthalate;

heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-3- phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,4-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline and its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-2,2,2-trichloro-1-(4-morpholinyl)-ethylformamide, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethyl-morpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]glutarimide, hexachlorobenzene, DL-methyl N-(2,6-dimethylphenyl)-N-furoyl(2)-alaninate, DL-methyl N-(2,6-dimethylphenyl)-N-(2'-methoxyacetyl)alaninate, N-(2,6-dimethylphenyl)-N-chloroacetyl-D,L-2-aminobutyrolactone, DL-methyl N-(2,6-dimethylphenyl)-N-(phenylacetyl)alaninate, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

The compounds of the formula I are furthermore useful for controlling pests from the classes of the insects, arachnids and nematodes. They can be employed as pesticides in crop protection, and in the hygiene, stored-product and veterinary sector.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be applied as such, in the form of their formulations or the use forms prepared therefrom, eg. in the form of directly sprayable solutions, powders, suspensions or dispersions, emulsions, oil dispersions, pastes, dusts, materials for spreading, and granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can vary within substantial ranges.

In general, they are from 0.0001 to 10%, preferably from 0.01 to 1%.

The active ingredients can also be employed very successfully in the ultra-low-volume method (ULV), it being possible to apply formulations comprising more than 95% by weight of active ingredient, or even the active ingredient without additives.

Under field conditions, the rate of active ingredient to be applied for controlling pests is from 0.1 to 2.0, preferably 0.2 to 1.0, kg/ha.

Substances which are suitable for preparing directly sprayable solutions, emulsions, pastes or oil dispersions are mineral oil fractions of medium to high boiling point, such as kerosene or diesel oil, furthermore coal tar oils, and oils of vegetable or animal origin, aliphatic, cyclic or aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, adhesive, dispersant or emulsifier. Alternatively, it is possible to prepare concentrates from active substance, wetting agent, adhesive, dispersant or emulsifier and, if desired, solvent or oil, which are suitable for dilution with water.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenyl, nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether, ethoxylated polyoxypropylene, lauryl alcohol polyglycol ether acetal, sorbitol ester, lignosulfite waste liquors and methylcellulose.

Powders, materials for spreading and dusts can be prepared by mixing or concomitantly grinding the active substances with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

Examples of formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil, which have been sprayed onto the surface of this silica gel. This gives a preparation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, and this gives a solution which is useful for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients to solid carriers. Examples of solid carriers are mineral earths such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas and products of vegetable origin such as cereal meal, tree bark meal, wood meal and nutshell meal, cellulose powders and other solid carriers.

Various types of oils, or herbicides, fungicides, other pesticides, and bactericides, can be added to the active ingredients, if appropriate also just before use (tank mix). These agents can be admixed with the agents according to the invention in a weight ratio of 1:10 to 10:1.

SYNTHESIS EXAMPLES

Example 1

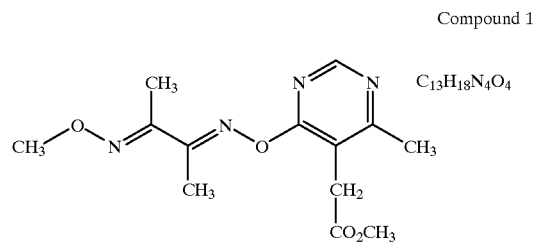

Compound 1

$C_{13}H_{18}N_4O_4$ 2 g (10.2 mmol) of methyl α-(4-chloro-6-methyl-5-pyrimidinyl)-acetate (for preparation cf. EP 634 405-A1) are stirred at 45° C. for 10 hours together with 2.0 g of potassium tert-butoxide and 1 g (10.2 mmol) of diacetyl monooxime in 80 ml of dimethylformamide. The mixture is then hydrolyzed with dil. hydrochloric acid, extracted with methyl tert-butyl ether (MtBE), and the combined org. phases are washed with water, dried and concentrated. The residue is treated with 60 ml of warm methanol, 1 g of O-methylhydroxylamine hydrochloride and 0.6 g of dry molecular sieve beads (3 Å) and the mixture is stirred at room temperature for four days. The solution is then filtered off, concentrated and partitioned between MtBE and water, and the organic phases are washed with water, dried and concentrated.

1.3 g of the title compound remain, which is employed without further purification in Example 2.

Example 2

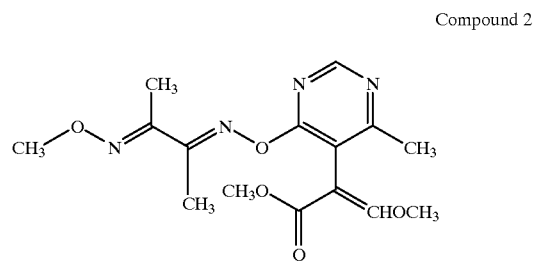

Compound 2

1.2 g (4 mmol) of the compound 1 from Example 1 are added at −40° C. to the solution from 1.95 g (16 mmol) of potassium tert-butoxide in 150 ml of dimethoxyethane. After 1 h, 15 ml of dimethylformamide-dimethylsulfate (1:1 adduct) are added, and the mixture is allowed to come to room temperature and is extracted with MtBE. The organic phases are washed with saturated sodium chloride solution, dried and concentrated. The residue is taken up in 50 ml of diethyl ether, treated with 0.5 g of p-toluenesulfonic acid and 3 ml of water and the mixture is subsequently stirred at room temperature for two days. It is then neutralized with solid sodium bicarbonate, extracted with ether, dried and concentrated again. The residue is taken up without further purification in 80 ml of dimethylformamide (DMF) and treated with cooling with 0.55 g (4 mol) of $K_2CO_3$ and 0.5 g (4 mmol) of dimethyl sulfate. The mixture is then stirred at room temperature for 3 h, extracted with MtBE, and the org. phases are dried over sodium sulfate and concentrated. The residue is chromatographed on silica gel using n-heptane/ethyl acetate (1:1) as an eluent. 0.7 g of the title compound 2 remains as a resin.

$^1$H-NMR (CDCl$_3$): 2.43 (s,3H); 3.74 (s,3H); 3.9 (3,H).

Examples of action against harmful fungi

It was possible to show the fungicidal action of the compounds of the formula I by the following tests:

Use Example 1—Activity against *Plasmopara viticola*

Leaves of potted vines of the Müller-Thurgau variety were sprayed with aqueous active compound preparation, which was prepared using a stock solution of 10% active compound, 63% cyclohexanone and 27% emulsifier, until dripping wet. In order to be able to assess the long-term effect of the substances, the plants were placed in a greenhouse for 7 days after the spray coating had dried on. Only then were the leaves inoculated with an aqueous zoospore suspension of *Plasmopara viticola*. The vines were then placed first for 48 hours in a water vapor-saturated chamber at 24° C. and then for 5 days in a greenhouse at from 20 to 30° C. After this time, the plants were again placed in a moist chamber for 16 hours to accelerate sporangiophore escape. The extent of the development of attack on the undersides of the leaves was then determined visually.

| Active compound | % attack on the leaves after application of aqueous active compound preparation containing 250 ppm |
|---|---|
| Table F, No. F.1 | 15 |
| Untreated | 70 |

Examples of action against animal pests

It was possible to show the action of the compounds of the general formula I against animal pests by the following tests:

The active compounds were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols)

and accordingly diluted to the desired concentration with acetone in the case of a) or with water in the case of b).

After conclusion of the tests, the lowest concentration in each case was determined at which the compounds still caused an 80–100% inhibition or mortality in comparison with untreated control tests (action threshold or minimum concentration).

We claim:

1. A pyrimidine compound I

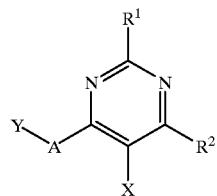

wherein

X is $C(CO_2CH_3)$=$NOCH_3$, $C(CONHCH_3)$=$NOCH_3$, $C(CO_2CH_3)$=$CHOCH_3$, $C(CO_2CH_3)$=$CHCH_3$ or $N(CO_2CH_3)$—$OCH_3$;

$R^1$ is hydrogen, $C_1$–$C_4$-alkyl, $C_1$–$C_4$-haloalkyl or $C_1$–$C_4$-alkoxy;

$R^2$ is hydrogen, $C_1$–$C_4$-alkyl or $C_1$–$C_4$-haloalkyl;

A is

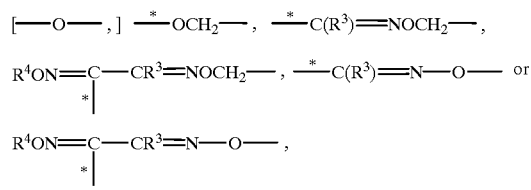

wherein the bond marked * is to Y;

$R^3$ is hydrogen, $C_1$–$C_4$-alkyl, $C_1$–$C_4$-haloalkyl, phenoxy-$C_1$–$C_4$-alkyl, $C_3$–$C_6$-cycloalkyl, cyano, $C_1$–$C_4$-alkoxy, hydroxyl or halogen;

$R^4$ is hydrogen, $C_1$–$C_8$-alkyl, $C_1$–$C_4$-haloalkyl, $C_1$–$C_6$-cyanoalkyl, $C_1$–$C_4$-alkoxy-$C_1$–$C_4$-alkyl, $C_2$–$C_4$-alkenyloxy-$C_1$–$C_4$-alkyl, $C_1$–$C_4$-haloalkoxy-$C_1$–$C_4$-alkyl, $C_1$–$C_4$-oxoalkyl, $C_2$–$C_4$-alkenyl, $C_2$–$C_4$-alkynyl, $C_2$–$C_4$-haloalkenyl, $C_2$–$C_4$-haloalkynyl, $C_3$–$C_6$-cycloalkyl, $C_3$–$C_6$-cycloalkyl-$C_1$–$C_4$-alkyl or $C_1$–$C_4$-alkoxy;

Y is hydrogen, hydroxyl, halogen, unsubstituted or substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio, and or a salt thereof.

2. A pyrimidine compound I

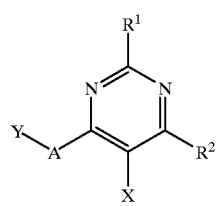

wherein

X is $C(CO_2CH_3)$=$NOCH_3$, $C(CONHCH_3)$=$NOCH_3$, $C(CO_2CH_3)$=$CHOCH_3$, $C(CO_2CH_3)$=$CHCH_3$ or $N(CO_2CH_3)$—$OCH_3$;

$R^1$ is hydrogen, $C_1$–$C_4$-alkyl, $C_1$–$C_4$-haloalkyl or $C_1$–$C_4$-alkoxy;

$R^2$ is hydrogen, $C_1$–$C_4$-alkyl or $C_1$–$C_4$-haloalkyl;

A is

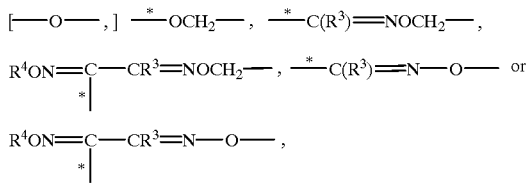

wherein the bond marked * is to Y;

$R^3$ is hydrogen, $C_1$–$C_4$-alkyl, $C_1$–$C_4$-haloalkyl, phenoxy-$C_1$–$C_4$-alkyl, $C_3$–$C_6$-cycloalkyl, cyano, $C_1$–$C_4$-alkoxy, hydroxyl or halogen;

$R^4$ is hydrogen, $C_1$–$C_8$-alkyl, $C_1$–$C_4$-haloalkyl, $C_1$–$C_6$-cyanoalkyl, $C_1$–$C_4$-alkoxy-$C_1$–$C_4$-alkyl, $C_2$–$C_4$-alkenyloxy-$C_1$–$C_4$-alkyl, $C_1$–$C_4$-haloalkoxy-$C_1$–$C_4$-alkyl, $C_1$–$C_4$-oxoalkyl, $C_2$–$C_4$-alkenyl, $C_2$–$C_4$-alkynyl, $C_2$–$C_4$-haloalkenyl, $C_2$–$C_4$-haloalkynyl, $C_3$–$C_6$-cycloalkyl, $C_3$–$C_6$-cycloalkyl-$C_1$–$C_4$-alkyl or $C_1$–$C_4$-alkoxy;

Y is hydrogen, hydroxyl, halogen, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy, $C_1$–$C_4$-alkoxy-$C_1$–$C_4$-alkyl, $C_3$–$C_6$-cycloalkoxy, $C_1$–$C_4$-alkylthio, $C_3$–$C_6$-cycloalkyl, $C_5$–$C_8$-cycloalkenyl, heterocyclyl, aryl, aryloxy, arylthio, aryl-$C_1$–$C_4$-alkyl, aryl-$C_2$–$C_4$-alkenyl, aryloxy-$C_1$–$C_4$-alkyl, aryl-$C_1$–$C_4$-alkoxy, hetaryl, hetaryloxy, hetarylthio, hetaryl-$C_1$–$C_4$-alkyl, hetarylthio-$C_1$–$C_4$-alkyl, hetaryl-$C_1$–$C_4$-alkoxy or hetaryl-$C_2$–$C_4$-alkenyl, wherein the cyclic radicals are unsubstituted or partially or completely halogenated and/or carry 1 to 3 of the following groups:

cyano, nitro, hydroxyl, mercapto, amino, formyl, carboxyl, aminocarbonyl, aminothiocarbonyl, $C_1$–$C_{12}$-alkyl, $C_1$–$C_6$-haloalkyl, $C_1$–$C_6$-hydroxyalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkylcarbonyl, $C_1$–$C_6$-alkylcarbonyloxy, $C_1$–$C_6$-alkoxycarbonyl, benzyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, C(=NOR$^b$)—Z$_n$—R$^c$, NR$^f$—CO—D—R$^9$, benzyl, benzyloxy, aryl, aryloxy, hetaryl or hetaryloxy, wherein the last 6 mentioned radicals are unsubstituted or partially or completely halogenated and/or carry 1 to 3 of the following groups: cyano, $C_1$–$C_6$-alkyl, $C_1$–$C_6$-alkoxycarbonyl, $C_1$–$C_4$-alkoxy, nitro, $C_1$–$C_6$-alkylcarbonyl, $C_1$–$C_6$-haloalkyl, hydroxyl, rhodano, formyl, aminocarbonylamino, methylsulfonylamino, aminocarbonyl and $C_1$–$C_6$-alkylaminocarbonyl;

Z is oxygen, sulfur or nitrogen, the nitrogen bearing hydrogen or $C_1$–$C_6$-alkyl;

D is a direct bond, oxygen or NR$^h$;

n is 0 or 1;

R$^b$ and R$^c$ independently of one another are hydrogen, $C_1$–$C_6$-alkyl, $C_2$–$C_6$-alkenyl, $C_2$–$C_6$-alkynyl or benzyl;

R$^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy or $C_1$–$C_6$-alkoxycarbonyl;

R$^g$ and R$^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl or hetaryl-$C_1$–$C_6$-alkyl, R$^9$ is hydrogen or $C_1$–$C_6$-alkyl;

or a salt thereof.

3. The compound I defined in claim 1, wherein $R^1$ is methyl and $R^2$ is hydrogen.

4. The compound I defined in claim 1, wherein $R^1$ is hydrogen and $R^2$ is methyl.

5. The compound I defined in claim 1, wherein $R^1$ is trifluoromethyl and $R^2$ is hydrogen.

6. The compound I defined in claim 1, wherein $R^1$ is hydrogen and $R^2$ is trifluoromethyl.

7. The compound I defined in claim 1, wherein $R^1$ and $R^2$ are hydrogen.

8. The compound I defined in claim 2, wherein $R^1$ is methyl and $R^2$ is hydrogen.

9. The compound I defined in claim 2, wherein $R^1$ is hydrogen and $R^2$ is methyl.

10. The compound I defined in claim 2, wherein $R^1$ is trifluoromethyl and $R^2$ is hydrogen.

11. The compound I defined in claim 2, wherein $R^1$ is hydrogen and $R^2$ is trifluoromethyl.

12. The compound I defined in claim 2, wherein $R^1$ and $R^2$ are hydrogen.

13. A pyrimidine compound of the formula

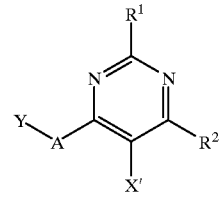

wherein

X' is C(=O)—CO$_2$CH$_3$, NO$_2$, NH—OH or N(OH)—CO$_2$CH$_3$;

$R^1$ is hydrogen, $C_1$–$C_4$-alkyl, $C_1$–$C_4$-haloalkyl or $C_1$–$C_4$-alkoxy;

$R^2$ is hydrogen, $C_1$–$C_4$-alkyl or $C_1$–$C_4$-haloalkyl;

A is

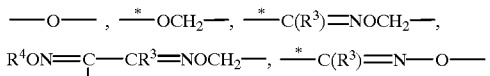

or

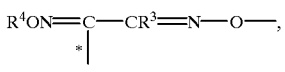

wherein the bond marked * is to Y;

$R^3$ is hydrogen, $C_1$–$C_4$-alkyl, $C_1$–$C_4$-haloalkyl, phenoxy-$C_1$–$C_4$-alkyl, $C_3$–$C_6$-cycloalkyl, cyano, $C_1$–$C_4$-alkoxy, hydroxyl or halogen;

$R^4$ is hydrogen, $C_1$–$C_8$-alkyl, $C_1$–$C_4$-haloalkyl, $C_1$–$C_6$-cyanoalkyl, $C_1$–$C_4$-alkoxy-$C_1$–$C_4$-alkyl, $C_2$–$C_4$-alkenyloxy-$C_1$–$C_4$-alkyl, $C_1$–$C_4$-haloalkoxy-$C_1$–$C_4$-alkyl, $C_1$–$C_4$-oxoalkyl, $C_2$–$C_4$-alkenyl, $C_2$–$C_4$-alkynyl, $C_2$–$C_4$-haloalkenyl, $C_2$–$C_4$-haloalkynyl, $C_3$–$C_6$-cycloalkyl, $C_3$–$C_6$-cycloalkyl-$C_1$–$C_4$-alkyl or $C_1$–$C_4$-alkoxy;

Y is hydrogen, hydroxyl, halogen, unsubstituted or substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio.

14. A pyrimidine compound of the formula

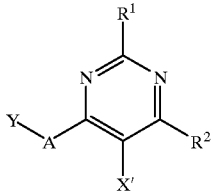

wherein
X' is C(=O)—CO$_2$CH$_3$, NO$_2$, NH—OH or N(OH)—CO$_2$CH$_3$;
R$^1$ is hydrogen, C$_1$–C$_4$-alkyl, C$_1$–C$_4$-haloalkyl or C$_1$–C$_4$-alkoxy;
R$^2$ is hydrogen, C$_1$–C$_4$-alkyl or C$_1$–C$_4$-haloalkyl;
A is

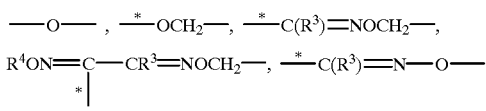

or

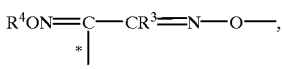

wherein the bond marked * is to Y;
R$^3$ is hydrogen, C$_1$–C$_4$-alkyl, C$_1$–C$_4$-haloalkyl, phenoxy-C$_1$–C$_4$-alkyl, C$_3$–C$_6$-cycloalkyl, cyano, C$_1$–C$_4$-alkoxy, hydroxyl or halogen;
R$^4$ is hydrogen, C$_1$–C$_8$-alkyl, C$_1$–C$_4$-haloalkyl, C$_1$–C$_6$-cyanoalkyl, C$_1$–C$_4$-alkoxy-C$_1$–C$_4$-alkyl, C$_2$–C$_4$-alkenyloxy-C$_1$–C$_4$-alkyl, C$_1$–C$_4$-haloalkoxy-C$_1$–C$_4$-alkyl, C$_1$–C$_4$-oxoalkyl, C$_2$–C$_4$-alkenyl, C$_2$–C$_4$-alkynyl, C$_2$–C$_4$-haloalkenyl, C$_2$–C$_4$-haloalkynyl, C$_3$–C$_6$-cycloalkyl, C$_3$–C$_6$-cycloalkyl-C$_1$–C$_4$-alkyl or C$_1$–C$_4$-alkoxy;
Y is hydrogen, hydroxyl, halogen, C$_1$–C$_4$-alkyl, C$_2$–C$_4$-alkenyl, C$_2$–C$_4$-alkynyl, C$_1$–C$_4$-haloalkyl, C$_1$–C$_4$-alkoxy, C$_1$–C$_4$-alkoxy-C$_1$–C$_4$-alkyl, C$_3$–C$_6$-cycloalkoxy, C$_1$–C$_4$-alkylthio, C$_3$–C$_6$-cycloalkyl, C$_5$–C$_8$-cycloalkenyl, heterocyclyl, aryl, aryloxy, arylthio, aryl-C$_1$–C$_4$-alkyl, aryl-C$_2$–C$_4$-alkenyl, aryloxy-C$_1$–C$_4$-alkyl, aryl-C$_1$–C$_4$-alkoxy, hetaryl, hetaryloxy, hetarylthio, hetaryl-C$_1$–C$_4$-alkyl, hetarylthio-C$_1$–C$_4$-alkyl, hetaryl-C$_1$–C$_4$-alkoxy or hetaryl-C$_2$–C$_4$-alkenyl, wherein the cyclic radicals are unsubstituted or partially or completely halogenated and/or carry 1 to 3 of the following groups:
cyano, nitro, hydroxyl, mercapto, amino, formyl, carboxyl, aminocarbonyl, aminothiocarbonyl, C$_1$–C$_{12}$-alkyl, C$_1$–C$_6$-haloalkyl, C$_1$–C$_6$-hydroxyalkyl, C$_1$–C$_6$-alkylsulfonyl, C$_1$–C$_6$-alkylsulfoxyl, C$_3$–C$_6$-cycloalkyl, C$_1$–C$_6$-alkoxy, C$_1$–C$_6$-haloalkoxy, C$_1$–C$_6$-alkylcarbonyl, C$_1$–C$_6$-alkylcarbonyloxy, C$_1$–C$_6$-alkoxycarbonyl, benzyloxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_2$–C$_6$-alkenyl, C$_2$–C$_6$-alkenyloxy, C(=NOR$^b$)—Z$_n$—R$^c$, NR$^f$—CO—D—R$^g$, benzyl, benzyloxy, aryl, aryloxy, hetaryl or hetaryloxy, wherein the last 6 mentioned radicals are unsubstituted or partially or completely halogenated and/or carry 1 to 3 of the following groups: cyano, C$_1$–C$_6$-alkyl, C$_1$–C$_6$-alkoxycarbonyl, C$_1$–C$_4$-alkoxy, nitro, C$_1$–C$_6$-alkylcarbonyl, C$_1$–C$_6$-haloalkyl, hydroxyl, rhodano, formyl, aminocarbonylamino, methylsulfonylamino, aminocarbonyl and C$_1$–C$_6$-alkylaminocarbonyl;
Z is oxygen, sulfur or nitrogen, the nitrogen bearing hydrogen or C$_1$–C$_6$-alkyl;
D is a direct bond, oxygen or NR$^h$;
n is 0 or 1;
R$^b$ and R$^c$ independently of one another are hydrogen, C$_1$–C$_6$-alkyl, C$_2$–C$_6$-alkenyl, C$_2$–C$_6$-alkynyl or benzyl;
R$^f$ is hydrogen, hydroxyl, C$_1$–C$_6$-alkyl, C$_2$–C$_6$-alkenyl, C$_2$–C$_6$-alkynyl, C$_1$–C$_6$-alkoxy, C$_2$–C$_6$-alkenyloxy, C$_2$–C$_6$-alkynyloxy, C$_1$–C$_6$-alkoxy-C$_1$–C$_6$-alkyl, C$_1$–C$_6$-alkoxy-C$_1$–C$_6$-alkoxy or C$_1$–C$_6$-alkoxycarbonyl;
R$^g$ and R$^h$ independently of one another are hydrogen, C$_1$–C$_6$-alkyl, C$_2$–C$_6$-alkenyl, C$_2$–C$_6$-alkynyl, C$_3$–C$_6$-cycloalkyl, C$_3$–C$_6$-cycloalkenyl, aryl, aryl-C$_1$–C$_6$-alkyl, hetaryl or hetaryl-C$_1$–C$_6$-alkyl, and
R$^9$ is hydrogen or C$_1$–C$_6$-alkyl.

15. The pyrimidine compound defined in claim 14, wherein X' is C(=O)—CO$_2$CH$_3$.

16. The pyrimidine compound defined in claim 14, wherein X' is NO$_2$, NH—OH or N(OH)—CO$_2$CH$_3$.

17. The pyrimidine compound defined in claim 14, wherein R$^1$ is methyl and R$^2$ is hydrogen.

18. The pyrimidine compound defined in claim 14, wherein R$^1$ is hydrogen and R$^2$ is methyl.

19. The pyrimidine compound defined in claim 14, wherein R$^1$ is trifluoromethyl and R$^2$ is hydrogen.

20. The pyrimidine compound defined in claim 14, wherein R$^1$ is hydrogen and R$^2$ is trifluoromethyl.

21. The pyrimidine compound defined in claim 14, wherein R$^1$ and R$^2$ are hydrogen.

22. A process for preparing a compound I

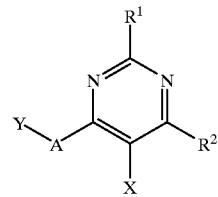

wherein
X is C(CO$_2$CH$_3$)=NOCH$_3$,
R$^1$ is hydrogen, C$_1$–C$_4$-alkyl, C$_1$–C$_4$-haloalkyl or C$_1$–C$_4$-alkoxy;
R$^2$ is hydrogen, C$_1$–C$_4$-alkyl or C$_1$–C$_4$-haloalkyl;
A is

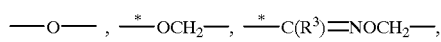

-continued

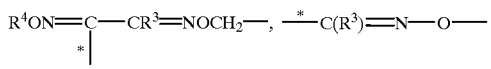

or

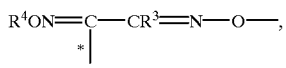

wherein the bond marked * is to Y;

$R^3$ is hydrogen, $C_1$–$C_4$-alkyl, $C_1$–$C_4$-haloalkyl, phenoxy-$C_1$–$C_4$-alkyl, $C_3$–$C_6$-cycloalkyl, cyano, $C_1$–$C_4$-alkoxy, hydroxyl or halogen;

$R^4$ is hydrogen, $C_1$–$C_8$-alkyl, $C_1$–$C_4$-haloalkyl, $C_1$–$C_6$-cyanoalkyl, $C_1$–$C_4$-alkoxy-$C_1$–$C_4$-alkyl, $C_2$–$C_4$-alkenyloxy-$C_1$–$C_4$-alkyl, $C_1$–$C_4$-haloalkoxy-$C_1$–$C_4$-alkyl, $C_1$–$C_4$-oxoalkyl, $C_2$–$C_4$-alkenyl, $C_2$–$C_4$-alkynyl, $C_2$–$C_4$-haloalkenyl, $C_2$–$C_4$-haloalkynyl, $C_3$–$C_6$-cycloalkyl, $C_3$–$C_6$-cycloalkyl-$C_1$–$C_4$-alkyl or $C_1$–$C_4$-alkoxy;

Y is hydrogen, hydroxyl, halogen, unsubstituted or substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio, which comprises reacting an α-oxopyrimidinylacetic acid IIa

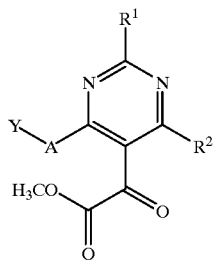

with methoxyamine or methoxyamine hydrohalide.

23. A process for preparing a compound I

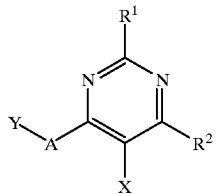

wherein

X is $C(CONHCH_3)=NOCH_3$, $R^1$ is hydrogen, $C_1$–$C_4$-alkyl, $C_1$–$C_4$-haloalkyl or $C_1$–$C_4$-alkoxy;

$R^2$ is hydrogen, $C_1$–$C_4$-alkyl or $C_1$–$C_4$-haloalkyl;

A is

-continued

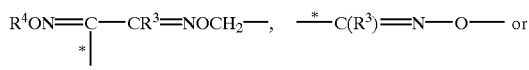

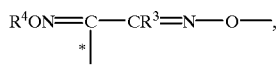

wherein the bond marked * is to Y;

$R^3$ is hydrogen, $C_1$–$C_4$-alkyl, $C_1$–$C_4$-haloalkyl, phenoxy-$C_1$–$C_4$-alkyl, $C_3$–$C_6$cycloalkyl, cyano, $C_1$–$C_4$-alkoxy, hydroxyl or halogen;

$R^4$ is hydrogen, $C_1$–$C_8$-alkyl, $C_1$–$C_4$-haloalkyl, $C_1$–$C_6$-cyanoalkyl, $C_1$–$C_4$-alkoxy-$C_1$–$C_4$-alkyl, $C_2$–$C_4$-alkenyloxy-$C_1$–$C_4$-alkyl, $C_1$–$C_4$-haloalkoxy-$C_1$–$C_4$-alkyl, $C_1$–$C_4$-oxoalkyl, $C_2$–$C_4$-alkenyl, $C_2$–$C_4$-alkynyl, $C_2$–$C_4$-haloalkenyl, $C_2$–$C_4$-haloalkynyl, $C_3$–$C_6$-cycloalkyl, $C_3$–$C_6$-cycloalkyl-$C_1$–$C_4$-alkyl or $C_1$–$C_4$-alkoxy;

Y is hydrogen, hydroxyl, halogen, unsubstituted or substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio, which comprises reacting a 2-oximinopyrimidinylacetic acid IIb

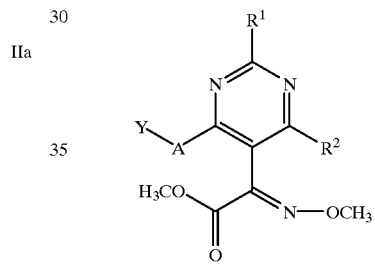

with methylamine.

24. A process for preparing a compound I

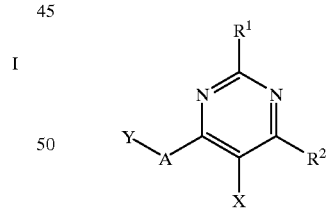

wherein

X is $C(CO_2CH_3)=CHOCH_3$ or $C(CO_2CH_3)=CHCH_3$, $R^1$ is hydrogen, $C_1$–$C_4$-alkyl, $C_1$–$C_4$-haloalkyl or $C_1$–$C_4$-alkoxy;

$R^2$ is hydrogen, $C_1$–$C_4$-alkyl or $C_1$–$C_4$-haloalkyl;

A is

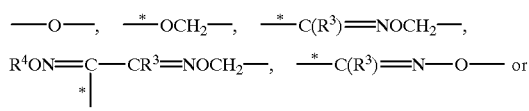

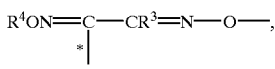

wherein the bond marked * is to Y;

R³ is hydrogen, $C_1$–$C_4$-alkyl, $C_1$–$C_4$-haloalkyl, phenoxy-$C_1$–$C_4$-alkyl, $C_3$–$C_6$-cycloalkyl, cyano, $C_1$–$C_4$-alkoxy, hydroxyl or halogen;

R⁴ is hydrogen, $C_1$–$C_8$-alkyl, $C_1$–$C_4$-haloalkyl, $C_1$–$C_6$-cyanoalkyl, $C_1$–$C_4$-alkoxy-$C_1$–$C_4$-alkyl, $C_2$–$C_4$-alkenyloxy-$C_1$–$C_4$-alkyl, $C_1$–$C_4$-haloalkoxy-$C_1$–$C_4$-alkyl $C_1$–$C_4$-oxoalkyl, $C_2$–$C_4$-alkenyl, $C_2$–$C_4$-alkynyl, $C_2$–$C_4$-haloalkenyl, $C_2$–$C_4$-haloalkynyl, $C_3$–$C_6$-cycloalkyl $C_3$–$C_6$-cycloalkyl-$C_1$–$C_4$-alkyl or $C_1$–$C_4$-alkoxy;

Y is hydrogen, hydroxyl, halogen, unsubstituted or substituted aryl, hetaryl, cycloalkyl, cycloalkenyl, heterocyclyl, alkyl, alkenyl, alkynyl, haloalkyl, alkoxy, aryloxy, arylthio, hetaryloxy, hetarylthio, cycloalkyloxy or alkylthio, and wherein A is not —O— when X is C(CO₂CH₃)=CHOCH₃, which comprises reacting an α-oxopyrimidinylacetic acid IIa

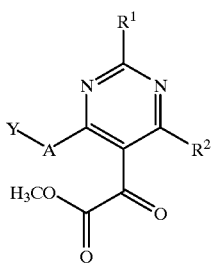

with a Wittig reagent IIc or IId

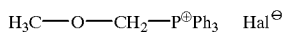

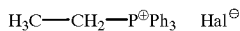

wherein Ph is phenyl and Hal is iodine, bromine, chlorine or fluorine.

25. A composition suitable for controlling animal pests or harmful fungi, comprising a compound I as defined in claim 1 or a salt thereof and at least one formulation auxiliary.

26. The composition defined in claim 22 wherein the animal pest is of the insects, arachnids or nematodes class.

27. A composition suitable for controlling animal pests or harmful fungi, comprising a compound I as defined in claim 2 or a salt thereof and at least one formulation auxiliary.

28. A method for controlling animal pests or harmful fungi, which comprises treating the pests or harmful fungi, their habitat or the plants, areas, materials or spaces to be kept free from them with an effective amount of a compound I as defined in claim 1 or a salt thereof.

29. A method for controlling animal pests or harmful fungi, which comprises treating the pests or harmful fungi, their habitat or the plants, areas, materials or spaces to be kept free from them with an effective amount of a compound I as defined in claim 2 or a salt thereof.

* * * * *

UNITED STATES PATENT AND TRADEMARK OFFICE
CERTIFICATE OF CORRECTION

PATENT NO. : 6,211,190 B1  
DATED : April 3, 2001  
INVENTOR(S) : Grammenos et al.

Page 1 of 1

It is certified that error appears in the above-identified patent and that said Letters Patent is hereby corrected as shown below:

Column 76, claim 1,
Line 24, delete "[–O–,]".

Column 77, claim 2,
Line 4, delete "[–O–,]".

Column 83, claim 24,
Line 16, insert a comma -- , -- between "cycloalkyl" and "$C_3$-$C_6$- cycloalkyl-$C_1$-$C_4$-alkyl".

Signed and Sealed this

Sixteenth Day of October, 2001

*Attest:*

NICHOLAS P. GODICI
*Attesting Officer*     *Acting Director of the United States Patent and Trademark Office*